US012590057B2

(12) United States Patent
Austin

(10) Patent No.: US 12,590,057 B2
(45) Date of Patent: Mar. 31, 2026

(54) CRYSTALLINE COMPLEXES

(71) Applicant: Theracryf PLC, Cheshire (GB)

(72) Inventor: Talbir Kaur Austin, Leicestershire (GB)

(73) Assignee: Theracryf PLC, Cheshire (GB)

(*) Notice: Subject to any disclaimer, the term of this patent is extended or adjusted under 35 U.S.C. 154(b) by 711 days.

(21) Appl. No.: 17/995,617

(22) PCT Filed: Apr. 8, 2021

(86) PCT No.: PCT/GB2021/050861
§ 371 (c)(1),
(2) Date: Oct. 6, 2022

(87) PCT Pub. No.: WO2021/205171
PCT Pub. Date: Oct. 14, 2021

(65) Prior Publication Data

US 2023/0322666 A1 Oct. 12, 2023

(30) Foreign Application Priority Data

Apr. 8, 2020 (GB) ..................................... 2005238

(51) Int. Cl.
*C07C 331/20* (2006.01)
*A61K 9/16* (2006.01)

(52) U.S. Cl.
CPC .......... *C07C 331/20* (2013.01); *A61K 9/1682* (2013.01); *C07B 2200/13* (2013.01)

(58) Field of Classification Search
CPC .... C07C 331/20; A61K 9/1682; A61K 9/205; A61K 45/06; A61K 31/26; A61K 47/6951; A61K 31/265; C07B 2200/13; A61P 35/00
See application file for complete search history.

(56) References Cited

U.S. PATENT DOCUMENTS

| | | | |
|---|---|---|---|
| 2008/0176942 | A1 | 7/2008 | Dagan et al. |
| 2015/0119359 | A1 | 4/2015 | Damireddi et al. |
| 2015/0191551 | A1 | 7/2015 | Damireddi et al. |
| 2019/0282534 | A1 | 9/2019 | Damireddi et al. |

FOREIGN PATENT DOCUMENTS

| | | | | | |
|---|---|---|---|---|---|
| CN | 104703628 | A | | 6/2015 | |
| CN | 108992675 | A | | 12/2018 | |
| EP | 2854861 | | | 4/2015 | |
| EP | 2854862 | | | 4/2015 | |
| EP | 3354267 | A1 | | 8/2018 | |
| WO | 2008091608 | A1 | | 7/2008 | |
| WO | 2013179056 | A1 | | 12/2013 | |
| WO | WO-2013179057 | A1 | * | 12/2013 | ............. A61P 35/00 |

OTHER PUBLICATIONS

Nakai Y, Yamamoto K, Terada K, Kajiyama A, Sasaki I. Properties of crystal water of .Alpha.-, .Beta.-, and .Gamma.-cyclodextrin. Chem Pharm Bull. 1986;34(5):2178-2182. (Year: 1986).*
John D. Clarke et al.; "Multi-targeted prevention of cancer by sulforaphane," Cancer Letters, vol. 269, No. 2, 2008, pp. 291-304.
James A. Clulow et al.; "Competition-based, quantitative chemical proteomics in breast cancer cells identifies new target profiles for sulforaphane," Chemical Communications, vol. 53, 2017, pp. 5182-5185.
Christine A. Houghton; "Sulforaphane: Its <<Coming of Age>> as a Clinically Relevant Nutraceutical in the Prevention and Treatment of Chronic Disease," Oxidative Medicine & Cellular Longevity, 2019, pp. 1-28.
Monia Lenzi et al.; "Sulforaphane as a Promising Molecule for Fighting Cancer," Cancer Treatment and Research, vol. 159, 2014, pp. 207-223.
Peng Liu et al.; "Sulforaphane exerts anti-angiogenesis effects against hepatocellular carcinoma through inhibition of STAT3/HIF-1α/VEGF signalling," Nature Scientific Reports, vol. 7, 2017, pp. s41598-017-12855-w.
Anna Pastore et al.; "Analysis of glutathione: implication in redox and detoxification," Clinica Chimica Acta, vol. 333, 2003, pp. 19-39.
H. Schmid et al.; "Synthese der racemischen und der optisch aktiven Formen des Sulforaphans," Helvetica Chimica Acta, vol. 31, issue 6, 1948, pp. 1497-1505.
Yuesheng Zhang et al.; "Discovery and development of sulforaphane as a cancer chemopreventive phytochemical," Acta Pharm. Sinica., vol. 28, No. 9, 2007, pp. 1343-1354.
International Search Report and Written Opinion issued on Jul. 16, 2021, for corresponding PCT Application No. PCT/GB2021/050861.
Search Report under Section 17 issued on Sep. 23, 2020, for corresponding GB Application No. GB2005238.7.
Fahey, J.W. et al., "Stabilized sulforaphane for clinical use: Phytochemical delivery efficiency," Molecular Nutrition and Food Research, vol. 61, No. 4, 2017, pp. 1600766 (1 of 10).

* cited by examiner

*Primary Examiner* — James H Alstrum-Acevedo
*Assistant Examiner* — Pierre Paul Eleniste
(74) *Attorney, Agent, or Firm* — POLSINELLI PC

(57) ABSTRACT

The present invention relates to crystalline complexes of sulforaphane and alpha-cyclodextrin; pharmaceutical compositions comprising the complexes; methods for their manufacture; and the use of said complexes as a medicament.

15 Claims, 17 Drawing Sheets

(A)

(B)

(A)

(B)

(A)

(B)

CRYSTALLINE COMPLEXES

CROSS-REFERENCE TO RELATED APPLICATIONS

This application is a national stage application (under 35 U.S.C. § 371) of PCT/GB2021/050861, filed Apr. 8, 2021, which claims benefit of GB Application No. 2005238.7, filed Apr. 8, 20202, which are incorporated herein by reference in their entireties.

The present invention relates to crystalline complexes of sulforaphane and alpha-cyclodextrin; pharmaceutical compositions comprising the complexes; methods for their manufacture; and the use of said complexes as a medicament.

BACKGROUND OF THE INVENTION

Sulforaphane is a compound derived from cruciferous vegetables such as cabbage, broccoli, broccoli sprouts; brussel sprouts, cauliflower, cauliflower sprouts; bok choy, kale, collards, arugula, kohlrabi, mustard, turnip, red raddish, and water cress. In the plant, it is present in bound form as glucoraphanin, a glucosinolate. In nature; sulforaphane is formed from glucoraphanin by the enzyme myrosinase following plant cell damage caused by, for example, chewing.

Racemic sulforaphane, also known as 4-methylsulfinylbutyl isothiocyanate, has the following structure:

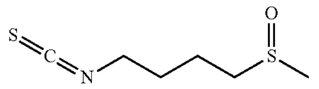

Naturally-occurring sulforaphane is chiral, existing predominantly in the (R) configuration.

Sulforaphane has been found over recent years to have multiple biological effects including the upregulation of glutathione leading to antioxidant and detoxification properties [Zhang & Tang, *Acta Pharm. Sinica* (2007); 1343-1354; Pastore et al., *Clinica Chimica Acta* (2003), 19-39]; activation of nuclear factor erythroid 2-related factor 2 (Nrf2) leading to anti-inflammatory and antiproliferative effects [Houghton, *Oxidative Medicine & Cellular Longevity* (2019), https://doi.org/10.1155/2019/2716870]; deactivation of signal transducer and activator of transcription 3 (STAT3) leading to anti-angiogenesis and apoptotic properties with relevance in the oncology field [Liu et al., *Nature Scientific Reports* (2017), doi: 10.1038/s41598-017-12855-w; Clarke et al., *Cancer Letters* (2008), 291-304; Lenzi et al., *Cancer Treat. Res*. (2014), 207-223], and as well as the binding of macrophage inhibitory factor (MIF) and nuclear factor kappa-light-chain enhancer of activated B cells (NF-κB) [Clulow et al., *Chem. Comm.* (2017), doi: 10.1039/c6cc08797c].

Despite the significant therapeutic potential of sulforaphane, its development as a pharmaceutical agent has been hindered by the inherent chemical instability of the compound. Sulforaphane exists in the form of an unstable oil which rapidly degrades under ambient conditions. This makes sulforaphane exceptionally hard to manufacture, formulate and distribute.

The complexation of sulforaphane with cyclodextrins has been shown to be a particularly effective approach to stabilise sulforaphane. WO 2008/091608 describes the synthesis of racemic sulforaphane and the preparation of stabilised complexes of sulforaphane with alpha-, beta- and gammaα-cyclodextrins. In the Examples section therein, different methods are described for the preparation of particular alpha-cyclodextrin complexes, with the highest loading of sulforaphane reported being 7.1 wt %, which equates to an approximate 1:2 molar ratio of sulforaphane to alpha-cyclodextrin. WO 2013/179057 describes improved scale-up procedures for the synthesis of sulforaphane and the production of complexes of sulforaphane and alpha-cyclodextrin. WO 2013/179056 discloses how sulforaphane:cyclodextrin complexes can be prepared by isolating chiral (R)-sulforaphane from a crude natural extract via cyclodextrin complexation.

In order to be suitable for large-scale, commercial manufacture, handling and storage a robust, reproducible and stable solid state form of stabilised sulforaphane is required.

The present invention is devised with the foregoing in mind.

SUMMARY OF INVENTION

Disclosed herein is a crystalline complex of sulforaphane and alpha-cyclodextrin having low water content and improved stability over a range of ambient humidity conditions. The complex may have long-term stability at temperatures up to and including 40° C. The complex may have long-term stability at relative humidities up to 70%.

According to a first aspect of the invention, there is provided a crystalline complex of sulforaphane and alpha-cyclodextrin having a water content of less than 8% why, wherein the crystalline form of the complex is stable between 0% and 60% relative humidity (RH) at 25° C.

According to a second aspect, there is provided a crystalline complex of sulforaphane and alpha-cyclodextrin (Form 3), wherein the crystalline form of the complex is characterised by X-Ray Powder Diffraction (XRPD) peaks at 5.3 and 10.7±0.2° 2θ, when measured in reflection mode.

According to a third aspect of the invention, there is provided a method for forming a crystalline complex of sulforaphane and alpha-cyclodextrin according to the first or second aspect, the method comprising the steps:

a) providing a complex of sulforaphane and alpha-cyclodextrin;
b) drying the complex from step a) with agitation of the complex at a pressure of less than 200 mbar, until the water content of the complex is less than 6% w/w.

According to a fourth aspect of the invention, there is provided a solid pharmaceutical composition comprising an effective amount of the crystalline complex according to the first or second aspect of the invention, and optionally at least one pharmaceutically acceptable excipient.

According to a fifth aspect of the invention, there is provided a crystalline complex according to the first or second aspect of the invention, or a pharmaceutical composition according to the fourth aspect of the invention, for use in therapy. In one embodiment, the crystalline complex or pharmaceutical composition is used in the treatment of diseases or disorders mediated by Nrf2 or STAT3. In one embodiment, the crystalline complex or pharmaceutical composition is used in the treatment of cancer, subarachnoid haemorrhage, intracerebral haemorrhage, ischemic stroke, delayed cerebral ischaemia, atherosclerosis, middle cerebral artery infarction, pulmonary arterial hypertension, Alport syndrome, non-alcoholic steatohepatitis, focal segmental glomerulosclerosis, Huntington's disease, Parkinson's disease, Alzheimer's disease, amyotrophic lateral sclerosis, liver cirrhosis, non-alcoholic fatty liver disease, hepatitis acute kidney injury, sepsis, chronic kidney disease, systemic lupus erythematosus nephritis, pulmonary emphysema, pulmonary fibrosis, chronic obstructive pulmonary disease, asthma, inflammatory lung disease, lymphocytic interstitial pneumonia, splenomegaly, type 1 diabetes, type 2 diabetes, diabetic nephropathy, diabetic retinopathy, diabetic cardiomyopathy, hyperglycaemia, arthritis, scleroderma, atopic dermatitis, lymphadenopathy, alopecia, hyperthyroidism, oesophageal achalasia, thrombocytopenia, neutropenia, autoimmune haemolytic anaemia, frontotemporal dementia, autism spectrum disorder, multiple sclerosis or Friedreich's ataxia. In a preferred embodiment, the cancer is breast cancer. In a separate embodiment, the cancer is glioma, such as glioblastoma multiforme.

According to a sixth aspect of the invention there is provided a crystalline complex according to the first or second aspect of the invention, or a pharmaceutical composition according to the fourth aspect of the invention, for use in therapy in combination with one or more additional therapeutic agents. In one embodiment, the therapy is the treatment of breast cancer and the additional therapeutic agents comprise an aromatase inhibitor, tamoxifen, exemestane, fuivestrant, oral SERDs or CDK4/6 inhibitors.

DETAILED DESCRIPTION

The disclosed complexes, compositions, processes of manufacture and methods may be understood more readily by reference to the following detailed description which form a part of this disclosure. It is to be understood that the disclosed complexes, compositions, processes of manufacture and methods are not limited to the specific complexes, compositions, processes of manufacture and methods described and/or shown herein, and that the terminology used herein is for the purpose of describing particular embodiments by way of example only and is not intended to be limiting of the claimed complexes, compositions, processes of manufacture and methods.

Reference to a particular numerical value includes at least that particular value, unless the context clearly dictates otherwise. When a range of values is expressed, another embodiment includes from the one particular value and/or to the other particular value. Further, reference to values stated in ranges include each and every value within that range. All ranges are inclusive and combinable.

When values are expressed as approximations, by use of the antecedent "about," it will be understood that the particular value forms another embodiment.

It is to be appreciated that certain features of the disclosed complexes, compositions, processes of manufacture and methods which are, for clarity, described herein in the context of separate embodiments, may also be provided in combination in a single embodiment. Conversely, various features of the disclosed complexes, compositions, processes of manufacture and methods that are, for brevity, described in the context of a single embodiment, may also be provided separately or in any sub-combination.

As used herein, the singular forms "a," "an," and "the" include the plural.

The term "about" when used in reference to numerical ranges, cut-offs, or specific values is used to indicate that the recited values may vary by up to as much as 10% from the listed value. As many of the numerical values used herein are experimentally determined, it should be understood by those skilled in the art that such determinations can, and often times will, vary among different experiments. The values used herein should not be considered unduly limiting by virtue of this inherent variation. Thus, the term "about" is used to encompass variations of ±10% or less, variations of ±5% or less, variations of ±1% or less, variations of ±0.5% or less, or variations of ±0.1% or less from the specified value.

As used herein, "treating" and like terms refer to reducing the severity and/or frequency of symptoms, eliminating symptoms and/or the underlying cause of said symptoms, reducing the frequency or likelihood of symptoms and/or their underlying cause, delaying, preventing and/or slowing the progression of diseases and/or disorders, such as cancers or benign proliferative disorders, and improving or remediating damage caused, directly or indirectly, by the diseases and/or disorders such as cancers or benign proliferative disorders.

As used herein, the phrase "therapeutically effective dose" refers to an amount of a composition comprising at least one active pharmaceutical ingredient, as described herein, effective to achieve a particular biological or therapeutic result such as, but not limited to, biological or therapeutic results disclosed, described, or exemplified herein. The therapeutically effective dose may vary according to factors such as the disease state, age, sex, and weight of the individual, and the ability of the composition to cause a desired response in a subject. Such results include, but are not limited to, the reduction, remission, and/or regression of the benign or malignant disease or prevention of the development of the benign or malignant disease, as determined by any means suitable in the art.

As used herein, "subject" includes a vertebrate, mammal, domestic animal or preferably a human being.

Crystalline Complexes

Previous preparations of 1:1 complexes of sulforaphane and alpha-cyclodextrin have succeeded in isolating crystalline material which existed as Form 1, wherein the material contained typically 8-15% w/w water, or as the higher hydrate Form 2 containing approximately 13-20% w/w water, or as a mixture of these forms. Crystalline complexes prepared analogously to the methods disclosed in WO 2013/179057 (Example 2) were found to be Form 1. The inventors have discovered a new crystalline form of the complex of sulforaphane and alpha-cyclodextrin (Form 3), which is less hygroscopic, has a lower water content and is surprisingly more physically stable over a wider range of humidity conditions. Additionally, although all the crystalline forms isolated of a complex of sulforaphane and alpha-cyclodextrin appear to be channel hydrates, Form 3 has surprisingly been found to have a more stable water content up to 60% RH at 25° C. Additional advantages which may be associated with the crystalline form of the present invention include high form purity (e.g. having a single physical form) which enables easier formulation, handling and storage of the complex; good compaction for tablet formation; and rapid dissolution in bio-relevant media.

According to a first aspect of the invention, there is provided a crystalline complex of sulforaphane and alpha-cyclodextrin having a water content of less than 8% w/w, wherein the crystalline form of the complex is stable between 0% and 60% relative humidity at 25° C.

In an embodiment, the crystalline complex is a channel hydrate. Therefore, there is provided a crystalline channel hydrate complex of sulforaphane and alpha-cyclodextrin having a water content of less than 8% w/w, wherein the crystalline form of the complex is stable between 0% and 60% relative humidity at 25° C.

The water content of a sample can be determined by any suitable means as will be apparent to one of skill in the art.

In one embodiment, the water content is determined by Karl-Fischer titration. In one embodiment, the water content is determined by thermogravimetric analysis (TGA). In one embodiment, the water content is determined by gravimetric vapour sorption (GVS). After formation of the crystalline complex according to the invention, the water content may be as low as 1-3% w/w. However, after exposure of the complex to ambient conditions (25° C., 40% RH) the material typically equilibrates (e.g. over a period of 3-7 days) to a water content of up to 5-7% w/w. It has been found, however, that Form 3, once equilibrated to 5-7% w/w water, maintains physical form at 60% RH making it unexpectedly stable over the 0% and 60% humidity range. Form 1 at 60% RH, however, shows an increased propensity to take up further water and to convert to a mixture of forms (e.g. Form 1 and Form 2).

In one embodiment, the crystalline complex has a water content of less than 7.5% w/w, less than 7.0% w/w, less than 6.5% w/w, less than 6.0% w/w, less than 5.5% w/w, less than 5.0% w/w, or less than 4.5% w/w. In a preferred embodiment, the crystalline complex has a water content of less than 7% w/w. In a more preferred embodiment, the crystalline complex has a water content of less than 6% w/w.

In an embodiment, the crystalline complex has a water content of 1.0 to 7.9% w/w, such as 1.5 to 7.5% w/w, 2.0 to 7.0% w/w, 2.5 to 7.5% w/w, 2.5 to 6.5% w/w, 2.5 to 6.0% w/w, 2.5 to 5.5% w/w, 3.0 to 8.0% w/w, 3.0 to 7.5% w/w, 3.0 to 6.5% w/w, 3.0 to 6.0% w/w, 3.0 to 5.5% w/w, 3.5 to 8.0% w/w, 3.5 to 7.5% w/w, 3.5 to 6.5% w/w, 3.5 to 6.0% w/w, 3.5 to 5.5% w/w, 4.0 to 8.0% w/w, 4.0 to 7.5% w/w, 4.0 to 6.5% w/w, 4.0 to 6.0% w/w, 4.0 to 5.5% w/w, 5.0 to 7.5% w/w, 5.0 to 7.0% w/w, 5.0 to 6.5% w/w, or 5.5 to 6.5% w/w. In an embodiment, the crystalline complex has a water content of 2.0 to 7.0% w/w.

In order to avoid the potential for increased formation of impurities it may be desirable to avoid excessive drying of the complex. Therefore, in a more preferred embodiment, the crystalline complex has a water content of 5.0 to 7.0% w/w, such as 5.5 to 6.5% w/w. In a preferred embodiment, the crystalline complex has a water content of about 6% w/w. In an embodiment, the water content as determined by thermogravimetric analysis (TGA) is less than 6% w/w. In an embodiment, the water content as determined by thermogravimetric analysis (TGA) is between 5.0 and 7.0% w/w, such as between 5.0 and 6.0% w/w.

As used herein, the crystalline form of the complex is 'stable' when the crystalline form does not convert to another form under the prescribed conditions. In other words, the stability is related to the physical stability of the solid state form. This may be assessed by X-ray powder diffraction (XRPD) of a sample of the complex carried out under the prescribed conditions. In an embodiment, the stability of the complex may be determined by variable humidity-XRPD, as described herein. In one embodiment, the crystalline form of the complex does not change between 0% and 60% relative humidity at 25° C., when a sample of the complex is analysed by variable humidity-XRPD. It may therefore be seen that the crystalline form according to the present invention has a wider stability domain compared to other forms of the complex. In one embodiment, the crystalline form of the complex is Form 3 and the complex does not convert to Form 1 between 0% and 60% relative humidity at 25° C., when a sample of the complex is analysed by variable humidity-XRPD. In one embodiment, the crystalline form of the complex is Form 3 and the complex does not convert to Form 2 between 0% and 60% relative humidity at 25° C., when a sample of the complex is analysed by variable humidity-XRPD.

In one embodiment, the physical form of a crystalline complex according to the present invention, does not change after at least 1 month storage at a temperature between 15° C. and 25° C. and an RH between 0% and 60%, when measured by XRPD. In a further embodiment, the physical form of a crystalline complex according to the present invention, does not change after at least 2 months (such as at least 3 months, at least 4 months, at least 5 months, or at least 6 months) storage at a temperature between 15° C. and 25° C. and an RH between 0% and 60%, when measured by XRPD. In another embodiment, the physical form of a crystalline complex according to the present invention, does not change after at least 1 month storage at about 40° C. and an RH between 0% and 60%, when measured by XRPD. In a further embodiment, the physical form of a crystalline complex according to the present invention, does not change after at least 2 months (such as at least 3 months, at least 4 months, at least 5 months, or at least 6 months) storage at about 40° C. and an RH between 0% and 60%, when measured by XRPD.

In another embodiment, the stability of the crystalline form according to the present invention may also refer to the chemical stability of sulforaphane contained with the complex, The sulforaphane purity may be assessed by high-performance liquid chromatography (HPLC) of a sample of the complex dissolved in water against an internal standard according to standard procedures known in the art. In one embodiment, the sulforaphane loading of a crystalline complex according to the present invention, is greater than 90% after at least 1 month storage at 15-25° C. and 0-60% RH, wherein loading refers to the sulforaphane purity by HPLC as a percentage of the purity measured at the start of the storage period (t=0). In a further embodiment, the sulforaphane loading of a crystalline complex according to the present invention, is greater than 90% after at least 2 months (such as at least 3 months, at least 4 months, at least 5 months, or at least 6 months) storage at 15-25° C. and 0-60% RH. In another embodiment, the sulforaphane loading of a crystalline complex according to the present invention, is greater than 90% after at least 1 month storage at 40° C. and 0-60% RH, wherein loading refers to the sulforaphane purity by HPLC as a percentage of the purity measured at the start of the storage period (t=0). In a further embodiment, the sulforaphane loading of a crystalline complex according to the present invention, is greater than 90% after at least 2 months (such as at least 3 months, at least 4 months, at least 5 months, or at least 6 months) storage at 40° C. and 0-60% RH. In another embodiment, the sulforaphane loading of a crystalline complex according to the present invention, is greater than 90% after at least 1 month storage in a closed container at 40° C. and 75% RH, wherein loading refers to the sulforaphane purity by HPLC as a percentage of the purity measured at the start of the storage period (t=0), In a further embodiment, the sulforaphane loading of a crystalline complex according to the present invention, is greater than 90% after at least 2 months (such as at least 3 months, at least 4 months, at least 5 months, or at least 6 months) storage in a closed container at 40° C. and 75% RH.

In one embodiment, a crystalline complex according to the first or second aspect of the present invention comprises less than 5% total related impurities by HPLC after at least 2 months (such as at least 3 months, at least 4 months, at least 5 months, or at least 6 months) storage at 5° C. Total related impurities refers to impurities which are related to sulforaphane and as the skilled person will appreciate does not refer to other components of the complex such as alpha-cyclodextrin, water or solvents. In one embodiment, a crystalline complex according to the present invention comprises less than 4% (such as less than 3%, less than 2% or less than 1.5%) total related impurities by HPLC after at least 2 months storage at 5° C.

In one embodiment, a crystalline complex according to the first or second aspect of the present invention comprises less than 5% total related impurities by HPLC after at least 2 months (such as at least 3 months, at least 4 months, at least 5 months, or at least 6 months) storage at 25° C. and 60% RH. In one embodiment, a crystalline complex according to the present invention comprises less than 4% (such as less than 3%, less than 2.5%, less than 2%, or less than 1.5%) total related impurities by HPLC after at least 2 months storage at 25° C. and 60% RH.

In an embodiment, a crystalline complex according to the first or second aspect of the present invention comprises less than 0.25% by HPLC area of a dimeric impurity having the following structure:

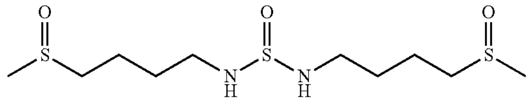

after at least 2 months (such as at least 3 months, at least 4 months, at least 5 months, or at least 6 months) storage at 5° C. In a convenient embodiment, the crystalline complex comprises less than 0.20% (such as less than 0.15%, less than 0.10% or less than 0.05%) by HPLC area of the dimeric impurity after at least 2 months storage at 5° C. In an embodiment, a crystalline complex according to the present invention comprises less than 0.40% by HPLC area of the dimeric impurity having the above structure after at least 2 months (such as at least 3 months, at least 4 months, at least 5 months, or at least 6 months) storage at 25° C. and 60% RH. In a convenient embodiment, the crystalline complex comprises less than 0.35% (such as less than 0.30%, less than 0.25%, less than 0.20%, less than 0.15%, or less than 0.10%) by HPLC area of the dimeric impurity after at least 2 months storage at 25° C. and 60% RH.

In an embodiment, a crystalline complex according to the first or second aspect of the present invention comprises less than 1% by HPLC area of an (α-cyclodextrin adduct after at least 2 months (such as at least 3 months, at least 4 months, at least 5 months, or at least 6 months) storage at 5° C. In a convenient embodiment, the crystalline complex comprises less than 0.8% (such as less than 0.7%, less than 0.6%, less than 0.5%, less than 0.4%, or less than 0.3%) by HPLC area of an α-cyclodextrin adduct after at least 2 months storage at 5° C. In an embodiment, a crystalline complex according to the present invention comprises less than 2.0% by HPLC area of an α-cyclodextrin adduct after at least 2 months (such as at least 3 months, at least 4 months, at least 5 months, or at least 6 months) storage at 25° C. and 60% RH. In a convenient embodiment, the crystalline complex comprises less than 1.5% (such as less than 1.25%, less than 1.0%, less than 0.80%, less than 0.70%, or less than 0.50%) by HPLC area of an α-cyclodextrin adduct after at least 2 months storage at 25° C. and 60% RH.

In an embodiment, a crystalline complex according to the first or second aspect of the present invention comprises less than 0.25% by HPLC area of the dimeric impurity shown above and less than 1% by HPLC area of an α-cyclodextrin adduct after at least 2 months (such as at least 3 months, at least 4 months, at least 5 months, or at least 6 months) storage at 5° C. In an embodiment, a crystalline complex according to the present invention comprises less than 0.40% by HPLC area of the dimeric impurity having the above structure and less than 2.0% by HPLC area of an α-cyclodextrin adduct after at least 2 months (such as at least 3 months, at least 4 months, at least 5 months, or at least 6 months) storage at 25° C. and 60% RH. In a preferred embodiment, the molar ratio of sulforaphane to alpha-cyclodextrin in the complex is in the range 0.8:1 to 1.2:1, such as in the range 0.9:1 to 1.1:1. In a more preferred embodiment, the molar ratio of sulforaphane to alpha-cyclodextrin in the complex is about 1:1. Preferably, the molar ratio of sulforaphane to alpha-cyclodextrin in the complex is 1:1. In an alternative embodiment, the molar ratio of sulforaphane to alpha-cyclodextrin in the complex is in the range 0.2:1 to 0.9:1, such as in the range 0.4:1 to 0.6:1, or about 0.5:1.

In a preferred embodiment, the sulforaphane present in the complex of the first aspect is racemic sulforaphane. Therefore, there is provided a crystalline complex of racemic sulforaphane and alpha-cyclodextrin having a water content of less than 8% w/w, wherein the crystalline form of the complex is stable between 0% and 60% relative humidity at 25° C. In an embodiment, there is provided a crystalline complex of racemic sulforaphane and alpha-cyclodextrin having a water content of less than 8% w/w, wherein the molar ratio of sulforaphane to alpha-cyclodextrin in the complex is in the range 0.9:1 to 1.1:1 and the crystalline form of the complex is stable between 0% and 60% relative humidity at 25° C. In an embodiment, there is provided a crystalline complex of racemic sulforaphane and alpha-cyclodextrin having a water content of less than 6% w/w, wherein the molar ratio of sulforaphane to alpha-cyclodextrin in the complex is 1:1 and the crystalline form of the complex is stable between 0% and 60% relative humidity at 25° C.

According to a second aspect of the invention, there is provided a crystalline complex of sulforaphane and alpha-cyclodextrin (Form 3), wherein the crystalline form of the complex is characterised by XRPD peaks at 5.3 and 10.7±0.2° 2θ, when measured in reflection mode.

Reference to Form 3 of the complex of sulforaphane and alpha-cyclodextrin as used herein refers to a complex having a molar ratio of sulforaphane to alpha-cyclodextrin of about 1:1.

The determination of the molar ratio is carried out according to $^{1}$H-NMR spectroscopy. Due to the inherent margin of error in calculating the ratio, the molar ratio of sulforaphane to alpha-cyclodextrin in the complex may be in the range 0.9:1 to 1.1:1.

The crystalline form of the complex may be analysed by XRPD in reflection mode or transmission mode. The crystalline form of the complex according to the second aspect is characterised by peaks at 5.3 and 10.7±0.2° 2θ, when measured by XRPD in reflection mode. In one embodiment, the crystalline complex according to the second aspect is further characterised by additional XRPD peaks at 8.1 and 16.1±0.2° 2θ, when measured in reflection mode.

In an embodiment, the crystalline complex of sulforaphane and alpha-cyclodextrin (Form 3) exhibits an X-ray powder diffraction pattern substantially the same as an X-ray powder diffraction pattern shown in FIG. 4 when measured at room temperature using Cu Kα radiation. In an embodiment, the crystalline complex of sulforaphane and alpha-cyclodextrin (Form 3) exhibits an X-ray powder diffraction pattern in reflection mode substantially the same as an X-ray powder diffraction pattern shown in FIG. 4A when measured at room temperature using Cu Kα radiation. In an embodiment, the crystalline complex of sulforaphane and alpha-cyclodextrin (Form 3) exhibits an X-ray powder diffraction pattern in transmission mode substantially the same as an X-ray powder diffraction pattern shown in FIG. 4B when measured at room temperature using Cu Kα radiation.

The term "substantially the same" with reference to XRPD means that variabilities in peak positions and relative intensities of the peaks are to be taken into account. For example, a typical precision if the 2θ values is in the range ±0.2° 2θ. A person skilled in the art will appreciate that relative peak intensities will show inter-apparatus variability, as well as variability due to the degree of crystallinity, preferred orientation, sample preparation and other factors known in the art.

In a preferred embodiment, there is provided a Form 3 crystalline complex of racemic sulforaphane and alpha-cyclodextrin, wherein the crystalline form of the complex is characterised by XRPD peaks at 5.3 and 10.7±0.2° 2θ, when measured in reflection mode. Most preferably, there is provided a crystalline complex of racemic sulforaphane and alpha-cyclodextrin, wherein the complex has a molar ratio of sulforaphane to alpha-cyclodextrin of about 1:1 and the complex is characterised by XRPD peaks at 5.3 and 10.7±0.2° 2θ, when measured in reflection mode. Most preferably, there is provided a crystalline complex of racemic sulforaphane and alpha-cyclodextrin, wherein the complex has a molar ratio of sulforaphane to alpha-cyclodextrin of about 1:1; a water content of less than 8% w/w (such as less than 6% w/w, or between 5% and 7% w/w); and the complex is characterised by XRPD peaks at 5.3 and 10.7±0.2° 2θ, when measured in reflection mode.

The crystalline complexes of the present invention may advantageously exist as a fine particulate form. When formed by a preferred process as described herein comprising agitated drying, the crystalline complexes according to the first or second aspect of the present invention are formed with low levels of agglomerated particles (typically referring herein to particles which are greater than 2000 μm (2 mm) in diameter). The degree of agglomeration may be determined by sieving a sample of material on a 2000 micron sieve and quantifying the oversize residue (% w/w) in relation to the input.

In an embodiment, there is provided a crystalline complex according to the present invention wherein the complex comprises less than 5% w/w of particles greater than 2000 μm in diameter. In an embodiment, there is provided a crystalline complex according to the present invention wherein the complex comprises less than 4.5% w/w (such as less than 4.0% w/w, less than 3.5% w/w, or less than 3.0% w/w) of particles greater than 2000 μm in diameter.

Process of Manufacture

In a third aspect, there is provided a method for forming a crystalline complex of sulforaphane and alpha-cyclodextrin according to the first or second aspect, the method comprising the steps:

a) providing a crystalline complex of sulforaphane and alpha-cyclodextrin;
b) drying the complex from step a) with agitation of the complex at a pressure of less than 200 mbar, until the water content of the complex is less than 6% w/w.

Sulforaphane can be derived from natural sources or prepared by synthetic procedures. Sulforaphane derived from natural sources is chiral, existing predominantly in the (R) configuration. In step a) the sulforaphane is preferably racemic sulforaphane. Racemic sulforaphane can be synthesised by various known methods, such as those disclosed by Schmid and Karrer (*Helvetica Chimica Acta* (1948), 1497), WO2008/091608 or WO2013/179057.

A complex of racemic sulforaphane and alpha-cyclodextrin can be prepared according to Example 1, or as disclosed in WO2013/179057. Typically the molar ratio of sulforaphane to alpha-cyclodextrin in the complex is about 1:1. In a preferred embodiment, step a) comprises providing a crystalline complex of racemic sulforaphane and alpha-cyclodextrin, the complex having a molar ratio of sulforaphane to alpha-cyclodextrin of 1:1.

In one embodiment, the crystalline complex of sulforaphane and alpha-cyclodextrin provided in step a) exists as Form 1. Form 1 is characterised by a peak at 9.8±0.2° 2θ, when measured by XRPD in reflection mode. Typically Form 1 contains 8-15% w/w water. In an embodiment, the crystalline complex of sulforaphane and alpha-cyclodextrin provided in step a) contains greater than 8% w/w water, such as greater than 10% w/w water, or greater than 12% w/w water. In an embodiment, the crystalline complex of sulforaphane and alpha-cyclodextrin provided in step a) contains 10-15% w/w water, such as 12-14% w/w water. In one embodiment, the crystalline complex of sulforaphane and alpha-cyclodextrin provided in step a) exists as Form 2. Form 2 is characterised by peaks at 9.5, 14.2 and 23.6±0.2° 2θ, when measured by XRPD in reflection mode. Typically Form 2 contains 13-20% w/w water. In one embodiment, the crystalline complex of sulforaphane and alpha-cyclodextrin provided in step a) exists as a mixture of Form 1 and Form 2.

It has been found that using very wet crystalline complex as the input material for the drying process may cause issues with balling or agglomeration during step b) of the process. Therefore, conveniently, the crystalline complex of sulforaphane and alpha-cyclodextrin provided in step a) has a water content of less than or equal to 25% w/w, such as less than 25% w/w, less than 24% w/w, less than 23% w/w, less than 22% w/w, less than 21% w/w, or less than 20% w/w. In an embodiment, the complex provided in step a) has a water content of 8 to 25% w/w, such as 10 to 25% w/w, 10 to 22% w/w, or 10 to 20% w/w.

Therefore, if the material provided in step a) has a water content greater than 25% w/w, then preferably the complex is dried without agitation for an initial period prior to step b), until the complex has a water content of less than or equal to 25% w/w, such as less than or equal to 20% w/w.

The drying in step b) is carried out at a pressure of less than 200 mbar. In a convenient embodiment, the drying in step b) is carried out at a pressure of less than 150 mbar, such as less than 100 mbar, less than 80 mbar or less than 75 mbar. In a most convenient embodiment, the drying in step b) is carried out at a pressure of about 50-70 mbar.

In an embodiment, the drying in step b) is carried out under inert gas flow. In a convenient embodiment, the inert gas is nitrogen. Conveniently, the inert gas (such as nitrogen) is provided at a flow rate of 0.1 to 1.0 L/min (such as 0.3 to 0.6 L/min, or 0.4 to 0.5 L/min).

The drying in step b) is carried out with agitation of the complex. Agitation may be carried out by any suitable means. Static (non-agitated) drying typically leads to less efficient formation of a crystalline form of the present invention, particularly on large scales where sample heterogeneity and particle agglomeration may be issues. In a preferred embodiment, the drying in step b) is carried out with constant or substantially constant agitation. 'Substantially constant' means that the agitation may be stopped for a short period to e.g. allow material to be removed to check the water content. In an embodiment, the drying in step b) is carried out with agitation for more than 80%, such more than 90% or more than 95% of the duration of the drying step.

In an embodiment, the agitation in step b) is provided at greater than 5 rpm. In a more convenient embodiment, the agitation is provided at greater than 10 rpm, such as 20 to 40 rpm. In a convenient embodiment the drying in step b) is carried out with overhead agitation. Overhead agitation may be used to stir a filter cake in a suitable drying apparatus, such as a Nutsche-type filter dryer. In a convenient embodiment, the overhead agitation is provided at greater than 5 rpm. In a more convenient embodiment, the overhead agitation is provided at greater than 10 rpm, such as 20 to 40 rpm.

In a preferred embodiment, the drying in step b) is carried out for at least 5 hours, such as at least 6 hours or at least 7 hours. In an embodiment, the drying in step b) is carried out for between 5 and 24 hours, such as between 5 and 12 hours, or between 7 and 12 hours. In an embodiment, the drying in step b) is carried out for about 9 to 10 hours.

Due to the potential for sulforaphane degradation at higher temperatures, it is convenient to carry out the drying at ambient temperatures. In a preferred embodiment, the drying in step b) is carried out at a temperature between 10° C. and 30° C. In an embodiment, the drying in step b) is carried out at a temperature between 10° C. and 25° C., or between 15° C. and 30° C., such as between 15° C. and 25° C., or about 20° C.

In an embodiment, the drying in step b) is carried out for 5 to 12 hours at a temperature between 10° C. and 30°. In an embodiment, the drying in step b) is carried out with substantially constant agitation for 5 to 12 hours at a temperature between 10° C. and 30°. In an embodiment, the drying in step b) is carried out with substantially constant agitation for 5 to 12 hours at a temperature between 10° C. and 30° under inert gas flow, In an embodiment, the drying in step b) is carried out with substantially constant agitation for 5 to 12 hours at a temperature between 10° C. and 30° under inert gas flow and at a pressure of less than 100 mbar.

The crystalline complexes of sulforaphane and alpha-cyclodextrin according to the invention contain less than 8% w/w water, such as 5-7% w/w water. In order to ensure conversion to a complex according to the present invention it is necessary to dry the complex from step a) until the water content of the complex is less than 6% w/w, In an embodiment, the drying in step b) is carried out until the water content of the complex is less than 5% w/w, such as less than 4% w/w, less than 3% w/w, or less than 2% w/w. In a preferred embodiment, the drying in step b) is carried out unto the water content of the complex is between 4% and 6% w/w, such as between 5% and 5.5% w/w.

Form 3 is characterised by a main XRPD peak at 10.7±0.2° 2θ, when measured in reflection mode. If the sample is over-dried (e.g. to less than approximately 4% w/w water), then the main XRPD peak may be at greater than 10.9° 2θ, when measured in reflection mode. However, after drying is completed, exposure of the complex to ambient conditions will result in a slow equilibration of the water content to approximately 5-7% w/w water and the main XRPD peak will then be concordant with 10.7±0.2° 2θ.

The drying process described above may be carried out more efficiently if the surface area of the complex is maximised. Accordingly, optionally prior to step b) the surface area of the crystalline complex may be increased by delumping and/or other comminution processing of the material. In an embodiment, prior to step b) the complex is subjected to a further processing step that increases the surface area of the complex (such as milling or grinding).

As can be seen from the large-scale formations of a complex of Form 3 as described in Example 5, without agitation, unless Form 1 was subjected to prolonged drying, optionally at an elevated temperature, under a sufficiently strong vacuum, then conversion to Form 3 did not occur. The filter drying trials described in Example 5B demonstrate that when the drying process is carried out with essentially constant agitation of the Form 1 complex, then Form 3 can be reproducibly obtained after drying under vacuum at ambient temperatures for less than 12 hours.

In an embodiment, there is provided a crystalline complex of sulforaphane and alpha-cyclodextrin obtainable by or obtained by a process as described herein.

In a specific embodiment, there is provided a crystalline complex of sulforaphane and alpha-cyclodextrin obtainable by or obtained by a process comprising the steps.

a) providing a crystalline complex of sulforaphane and alpha-cyclodextrin;
b) drying the complex from step a) with substantially constant agitation at a temperature between 10° C. and 30° under inert gas flow and at a pressure of less than 100 mbar, until the water content of the complex is less than 6% w/w.

Compositions

According to a fourth aspect of the invention, there is provided a solid pharmaceutical composition comprising an effective amount of the crystalline complex according to the first or second aspect of the invention, and optionally at least one pharmaceutically acceptable excipient In an embodiment, the pharmaceutical composition comprises a crystalline complex of sulforaphane and alpha-cyclodextrin, wherein greater than 50% of the complex is characterised by XRPD peaks at 5.3 and 10.7±0.2° 2θ, when measured in reflection mode. Preferably, greater than 55%, greater than 60%, greater than 65%, greater than 75%, greater than 80% or greater than 85% of the complex is characterised by XRPD peaks at 5.3 and 10.7±0.2° 2θ, when measured in reflection mode. In a most preferred embodiment, greater than 90% of the complex is characterised by XRPD peaks at 5.3 and 10.7±0.2° 2θ, when measured in reflection mode. The percentage of the complex present in a given form may be approximated by XRPD or Raman spectroscopy following the construction of a calibration curve.

Over-drying of Form 3 may result in the complex having a compressed Form 3 crystalline structure (e.g. reduced distance between crystal lattice layers). Such compressed Form 3 may have a main XRPD peak at 10.9±0.2° 2θ, when measured in reflection mode. As the compressed Form 3 tends to gradually equilibrate back to Form 3 unless kept under anhydrous conditions, mixtures of Form 3 and compressed Form 3 have the potential to deliver the beneficial properties of Form 3 described herein. In an embodiment, the pharmaceutical composition comprises a crystalline complex of sulforaphane and alpha-cyclodextrin, wherein the complex comprises a mixture of Form 3 and compressed Form 3. In an embodiment, the pharmaceutical composition comprises a crystalline complex of sulforaphane and alpha-cyclodextrin, wherein the complex is characterised by XRPD peaks at 10.7 and 10.9±0.2° 2θ, when measured in reflection mode, In an embodiment, greater than 60% of the complex is Form 3 (XRPD main peak at 10.7±0.2° 2θ) and less than 40% is compressed Form 3 (XRPD main peak at 10.9±0.2° 2θ). Suitably, greater than 80% of the complex is Form 3 (XRPD main peak at 10.7±0.2° 2θ) and less than 20% is compressed Form 3 (XRPD main peak at 10.9±0.2° 2θ).

The pharmaceutical compositions according to the present invention may be administered by any suitable means, as may be determined by a skilled person on the basis of the disease or disorder being treated with the composition.

The solid compositions of the invention may be in a form suitable for oral use (for example as tablets, lozenges, hard or soft capsules, dispersible powders or granules), for administration by inhalation (for example as a finely divided powder), or for administration by insufflation (for example as a finely divided powder). Preferably, the solid pharmaceutical composition is for oral administration.

The compositions of the invention may be obtained by conventional procedures using conventional pharmaceutical excipients, well known in the art. Thus, compositions intended for oral use may contain, for example, one or more colouring, sweetening, flavouring and/or preservative agents.

As used herein, "pharmaceutically acceptable excipient" means a pharmaceutically acceptable material, composition or vehicle involved in giving form or consistency to the pharmaceutical composition. Each excipient must be compatible with the other ingredients of the pharmaceutical composition when comingled such that interactions which would substantially reduce the efficacy of the complex of the invention when administered to a patient and interactions which would result in pharmaceutical compositions that are not pharmaceutically acceptable are avoided. In addition, each excipient must of course be of sufficiently high purity to render it pharmaceutically acceptable.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting of the complex of the invention or sulforaphane, once administered to the patient, from one organ, or portion of the body, to another organ, or portion of the body. Certain pharmaceutically acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

The pharmaceutical compositions of the invention are prepared using techniques and methods known to those skilled in the art. Some of the methods commonly used in the art are described in Remington's Pharmaceutical Sciences (Mack Publishing Company).

An effective amount of the complex of the present invention for use in therapy of a disease or disorder is an amount sufficient to symptomatically relieve in a warm-blooded animal, particularly a human, the symptoms of the disease or disorder, to slow the progression of the disease or disorder, or to reduce in patients with symptoms of the disease or disorder the risk of getting worse.

The amount of the active complex that is combined with one or more excipients to produce a single dosage form will necessarily vary depending upon the host treated and the particular route of administration. For example, a formulation intended for oral administration to humans will generally contain, for example, from 0.5 mg to 1.0 g of active complex (more suitably from 100 to 500 mg, for example from 300 mg) compounded with an appropriate and convenient amount of excipients which may vary from about 5 to about 98 percent by weight of the total composition.

The size of the dose for therapeutic or prophylactic purposes of the complex of the invention will naturally vary according to the nature and severity of the conditions, subject age, weight, gender, diet and the route of administration, according to well-known principles of medicine.

In using a complex of the invention for therapeutic or prophylactic purposes it will generally be administered so that a daily dose in the range, for example, 0.1 mg/kg to 75 mg/kg body weight is received, given if required in divided doses. Oral administration may be suitable, particularly in tablet form. Typically, unit dosage forms will contain about 0.5 mg to 1.0 g of a complex of this invention. In a preferred embodiment, the unit dosage form of the composition contains about 100 mg to 500 mg, such as about 200 mg to 400 mg of a complex of the invention. In a most preferred embodiment, the unit dosage form of the composition contains about 300 mg of a complex of the invention. The unit dosage form for oral administration may be a tablet or a capsule. In a preferred embodiment, the solid pharmaceutical composition according to the present invention is formulated as a tablet. In an alternative preferred embodiment, the solid pharmaceutical composition according to the present invention is formulated as a capsule.

Daily doses may be given as a single administration. Alternatively, administration may be twice or more times during a day. As an example, the pharmaceutical compositions (e.g. as a tablet or a capsule) may be orally administered at least once a day, such as once a day, or such as twice a day.

Suitable amounts of the active complex to be given as a daily dose are of about 1 mg to about 5 g, such as about 1 mg to about 1 g, such as about 5 mg to about 2 g, such as about 10 mg to about 1 g, such as about 5 mg to about 500 mg, such as about 10 mg to about 500 mg, such as about 10 mg to about 400 mg, such as about 200 mg to about 400 mg, such as about 250 mg to about 350 mg, such as about 280 mg to about 320 mg, such as about 290 mg to about 310 mg, such as about 300 mg, such as 300 mg, such as about 50 mg to about 900 mg, such as about 100 mg to about 800 mg, such as about 300 mg to about 700 mg, such as about 500 mg to about 700 mg, such as about 600 mg, or such as 600 mg.

Medical Uses

According to a fifth aspect of the invention, there is provided a crystalline complex according to the first or second aspect of the invention, or a pharmaceutical composition according to the fourth aspect of the invention, for use in therapy.

In one embodiment, there is provided a crystalline complex according to the first or second aspect of the invention, or a pharmaceutical composition according to the fourth aspect of the invention for use as a medicament.

In one embodiment, the pharmaceutical composition is for use as a medicament wherein the pharmaceutical composition is administered orally.

In one embodiment, the complex or the pharmaceutical compositions are useful in the treatment and/or prevention of diseases and/or disorders. In one embodiment, there is provided a crystalline complex according to the first or second aspect of the invention, or a pharmaceutical composition according to the fourth aspect of the invention, for use in the treatment of diseases or disorders mediated by Nrf2 or STAT3. In one embodiment, there is provided a crystalline complex according to the first or second aspect of the invention, or a pharmaceutical composition according to the fourth aspect of the invention, for use in the treatment of diseases or disorders mediated by Nrf2 activation or STAT3 deactivation.

In another embodiment, the present invention relates to the use of a complex or composition of the invention as defined herein, in the manufacture of a medicament for use in the treatment of diseases or disorders mediated by Nrf2 activation or STAT3 deactivation.

In another embodiment, the present invention relates to a method of treating a disease or disorders mediated by Nrf2 activation or STAT3 deactivation, said method comprising administering to a subject in need of such treatment a therapeutically effective amount of a complex or composition of the invention as defined herein.

In one embodiment, there is provided a crystalline complex according to the first or second aspect of the invention, or a pharmaceutical composition according to the fourth aspect of the invention, for use in the treatment of cancer, subarachnoid haemorrhage, intracerebral haemorrhage, ischemic stroke, delayed cerebral ischaemia, atherosclerosis, middle cerebral artery infarction, pulmonary arterial hypertension, Alport syndrome, non-alcoholic steatohepatitis, focal segmental glomerulosclerosis, Huntington's disease, Parkinson's disease, Alzheimer's disease, amyotrophic lateral sclerosis, liver cirrhosis, non-alcoholic fatty liver disease, hepatitis acute kidney injury, sepsis, chronic kidney disease, systemic lupus erythematosus nephritis, pulmonary emphysema, pulmonary fibrosis, chronic obstructive pulmonary disease, asthma, inflammatory lung disease, lymphocytic interstitial pneumonia, splenomegaly, type 1 diabetes, type 2 diabetes, diabetic nephropathy, diabetic retinopathy, diabetic cardiomyopathy, hyperglycaemia, arthritis, scleroderma, atopic dermatitis, lymphadenopathy, alopecia, hyperthyroidism, oesophageal achalasia, thrombocytopenia, neutropenia, autoimmune haemolytic anaemia, frontotemporal dementia, autism spectrum disorder, multiple sclerosis or Friedreich's ataxia.

In an embodiment, there is provided a complex or a composition of the invention as defined herein, for use in the treatment of cancer, subarachnoid haemorrhage, intracerebral haemorrhage, ischemic stroke, delayed cerebral ischaemia, pulmonary arterial hypertension, Alport syndrome, non-alcoholic steatohepatitis, focal segmental glomerulosclerosis, Huntington's disease, Parkinson's disease, Alzheimer's disease, amyotrophic lateral sclerosis, frontotemporal dementia, autism spectrum disorder, multiple sclerosis or Friedreich's ataxia.

In another embodiment, the present invention relates to the use of a complex or composition of the invention as defined herein, in the manufacture of a medicament for use in the treatment of cancer, subarachnoid haemorrhage, intracerebral haemorrhage, ischemic stroke, delayed cerebral ischaemia, atherosclerosis, middle cerebral artery infarction, pulmonary arterial hypertension, Alport syndrome, non-alcoholic steatohepatitis, focal segmental glomerulosclerosis, Huntington's disease, Parkinson's disease, Alzheimer's disease, amyotrophic lateral sclerosis, liver cirrhosis, non-alcoholic fatty liver disease, hepatitis acute kidney injury, sepsis, chronic kidney disease, systemic lupus erythematosus nephritis, pulmonary emphysema, pulmonary fibrosis, chronic obstructive pulmonary disease, asthma, inflammatory lung disease, lymphocytic interstitial pneumonia, splenomegaly, type 1 diabetes, type 2 diabetes, diabetic nephropathy, diabetic retinopathy, diabetic cardiomyopathy, hyperglycaemia, arthritis, scleroderma, atopic dermatitis, lymphadenopathy, alopecia, hyperthyroidism, oesophageal achalasia, thrombocytopenia, neutropenia, autoimmune haemolytic anaemia, frontotemporal dementia, autism spectrum disorder, multiple sclerosis or Friedreich's ataxia.

In another embodiment, the present invention relates to a method of treating cancer, subarachnoid haemorrhage, intracerebral haemorrhage, ischemic stroke, delayed cerebral ischaemia, atherosclerosis, middle cerebral artery infarction, pulmonary arterial hypertension, Alport syndrome, non-alcoholic steatohepatitis, focal segmental glomerulosclerosis, Huntington's disease, Parkinson's disease, Alzheimer's disease, amyotrophic lateral sclerosis, liver cirrhosis, non-alcoholic fatty liver disease, hepatitis acute kidney injury, sepsis, chronic kidney disease, systemic lupus erythematosus nephritis, pulmonary emphysema, pulmonary fibrosis, chronic obstructive pulmonary disease, asthma, inflammatory lung disease, lymphocytic interstitial pneumonia, splenomegaly, type 1 diabetes, type 2 diabetes, diabetic nephropathy, diabetic retinopathy, diabetic cardiomyopathy, hyperglycaemia, arthritis, scleroderma, atopic dermatitis, lymphadenopathy, alopecia, hyperthyroidism, oesophageal achalasia, thrombocytopenia, neutropenia, autoimmune haemolytic anaemia, frontotemporal dementia, autism spectrum disorder, multiple sclerosis or Friedreich's ataxia, the method comprising administering to a subject in need of such treatment a therapeutically effective amount of a complex or composition of the invention as defined herein.

In one embodiment, there is provided a crystalline complex according to the first or second aspect of the invention, or a pharmaceutical composition according to the fourth aspect of the invention, for use in the treatment of cancer, subarachnoid haemorrhage, delayed cerebral ischaemia, non-alcoholic steatohepatitis, or autism spectrum disorder.

In another embodiment, the present invention relates to the use of a complex or composition of the invention as defined herein, in the manufacture of a medicament for use in the treatment of cancer, subarachnoid haemorrhage, delayed cerebral ischaemia, non-alcoholic steatohepatitis, or autism spectrum disorder.

In another embodiment, the present invention relates to a method of treating cancer, subarachnoid haemorrhage, delayed cerebral ischaemia, non-alcoholic steatohepatitis, or autism spectrum disorder, the method comprising administering to a subject in need of such treatment a therapeutically effective amount of a complex or composition of the invention as defined herein.

The cancer to be treated may be a solid tumour (such as breast cancer, colorectal cancer, lung cancer, liver cancer, bladder cancer, cervical cancer, hepatocellular carcinoma, squamous cell carcinoma, melanoma, glioma, head and neck cancer, pancreatic cancer or prostate cancer) or a blood cancer (such as leukaemia, acute lymphoblastic leukaemia, juvenile myelomonocytic leukaemia, non-Hodgkin lymphoma or diffuse large B-cell lymphoma). In a preferred embodiment, the cancer is breast cancer. In a most preferred embodiment, the breast cancer is ER+ or HER2− metastatic breast cancer. In an alternative embodiment, the cancer is glioma, such as high grade glioma or glioblastoma multiforme.

Combinations

The complexes and compositions of the invention may be used to prevent or treat diseases or disorders as a monotherapy, or in combination with other compounds or treatments.

Therefore, according to a sixth aspect of the invention, there is provided a crystalline complex according to the first or second aspect of the invention, or a pharmaceutical composition according to the fourth aspect of the invention, for use in therapy in combination with one or more additional therapeutic agents, The selection of the one or more additional therapeutic agents will of course vary depending on the disease or condition to be treated and its severity.

It is commonplace to use combination therapies to treat certain medical conditions.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

In one embodiment, there is provided a combination suitable for use in the treatment of a disease or condition in which Nrf2 activation or STAT3 deactivation is implicated, comprising a complex or composition of the invention as defined hereinbefore, and another therapeutic agent.

In an embodiment, there is provided a combination suitable for use in the prevention or treatment of cancer, subarachnoid haemorrhage, intracerebral haemorrhage, ischemic stroke, delayed cerebral ischaemia, pulmonary arterial hypertension, Alport syndrome, non-alcoholic steatohepatitis, focal segmental glomerulosclerosis, Huntington's disease, Parkinson's disease, Alzheimer's disease, amyotrophic lateral sclerosis, frontotemporal dementia, autism spectrum disorder, multiple sclerosis or Friedreich's ataxia, the combination comprising a complex or composition of the invention as defined hereinbefore, and one or more additional therapeutic agents.

In an embodiment, there is provided a crystalline complex according to the first or second aspect of the invention, or a pharmaceutical composition according to the fourth aspect of the invention, for use in the treatment of cancer in combination with one or more additional therapeutic agents and/or in combination with one or more additional treatments (e.g. radiotherapy).

In an embodiment, there is provided a crystalline complex according to the first or second aspect of the invention, or a pharmaceutical composition according to the fourth aspect of the invention, for use in the treatment of breast cancer in combination with one or more additional therapeutic agents selected from an aromatase inhibitor, tamoxifen, exemestane, fulvestrant, an oral SERD or a CDK4/6 inhibitor.

In an embodiment, there is provided a combination suitable for use in the prevention or treatment of breast cancer, the combination comprising a complex or composition of the invention as defined hereinbefore, and one or more additional therapeutic agents selected from an aromatase inhibitor, tamoxifen, exemestane, fulvestrant, an oral SERD or a CDK4/6 inhibitor.

In an embodiment, there is provided a crystalline complex according to the first or second aspect of the invention, or a pharmaceutical composition according to the fourth aspect of the invention, for use in the treatment of glioma (such as glioblastoma multiforme) in combination with one or more one or more of radiotherapy and temozolomide.

In an embodiment, there is provided a combination suitable for use in the prevention or treatment of glioma (such as glioblastoma multiforme), the combination comprising a complex or composition of the invention as defined hereinbefore, and one or more of radiotherapy and temozolomide.

The following numbered statements are not claims, but refer to certain aspects and embodiments of the present disclosure:

1. A crystalline complex of sulforaphane and alpha-cyclodextrin having a water content of less than 8% w/w, wherein the crystalline form of the complex is stable between 0% and 60% relative humidity at 25° C.
2. The crystalline complex according to statement 1 having a water content of less than 6% w/w.
3. The crystalline complex according to statement 1 or statement 2, wherein the molar ratio of sulforaphane to alpha-cyclodextrin in the complex is in the range 0.9:1 to 1.1:1.
4. The crystalline complex according to statement 1 or statement 2, wherein the molar ratio of sulforaphane to alpha-cyclodextrin in the complex is about 1:1.
5. A crystalline complex of sulforaphane and alpha-cyclodextrin (Form 3), wherein the crystalline form of the complex is characterised by XRPD peaks at 5.3 and 10.7±0.2° 2θ, when measured in reflection mode.
6. The crystalline complex according to statement 5, further characterised by further XRPD peaks at 8.1 and 16.1±0.2° 2θ, when measured in reflection mode.
7. The crystalline complex according to statement 5 that exhibits an X-ray powder diffraction pattern substantially the same as the X-ray powder diffraction pattern shown in FIG. 4 when measured at room temperature using Cu Kα radiation.
8. A method for forming a crystalline complex of sulforaphane and alpha-cyclodextrin according to any one of statements 1 to 7, the method comprising the steps:
   a) providing a complex of sulforaphane and alpha-cyclodextrin;
   b) drying the complex from step a) at a temperature of greater than or equal to 25° C. and at a pressure of less than 50 mbar for at least 12 hours, until the water content of the complex is less than 6% w/w.

9. The method according to statement 8, wherein the drying in step b) is carried out at a pressure of less than 10 mbar.
10. The method according to statement 8 or statement 9, wherein the drying in step b) is carried out for at least 18 hours.
11. The method according to statements 8 to 10, wherein the drying in step b) is carried out a temperature between 25° C. and 30° C. for 24 to 200 hours.
12. The method according to statements 8 to 11, wherein prior to step b) the complex is subjected to a further processing step that increases the surface area of the complex.
13. A crystalline complex of sulforaphane and alpha-cyclodextrin obtained by the method of any one of statements 8 to 12.
14. A solid pharmaceutical composition comprising an effective amount of the crystalline complex according to any one of statements 1 to 7 or 13, and optionally at least one pharmaceutically acceptable excipient.
15. The solid pharmaceutical composition according to statement 14, wherein greater than 50% of the crystalline complex of sulforaphane and alpha-cyclodextrin is characterised by XRPD peaks at 5.3 and 10.7±0.2° 2θ, when measured in reflection mode.
16. The solid pharmaceutical composition according to statement 14, wherein greater than 80%, such as greater than 90%, of the crystalline complex of sulforaphane and alpha-cyclodextrin is characterised by XRPD peaks at 5.3 and 10.7±0.2° 2θ, when measured in reflection mode.
17. The solid pharmaceutical composition according to statements 14 to 16, wherein the composition is formulated as a tablet.
18. The solid pharmaceutical composition according to statements 14 to 16, wherein the composition is formulated as a capsule.
19. A complex according to statements 1 to 7 or 13, or a pharmaceutical composition according to claims 14 to 18, for use in therapy.
20. A complex according to statements 1 to 7 or 13, or a pharmaceutical composition according to claims 14 to 18, for use in the treatment of diseases or disorders mediated by Nrf2 or STAT3.
21. A complex according to statements 1 to 7 or 13, or a pharmaceutical composition according to claims 14 to 18, for use in the treatment of in the treatment of cancer, subarachnoid haemorrhage, intracerebral haemorrhage, ischemic stroke, delayed cerebral ischaemia, atherosclerosis, middle cerebral artery infarction, pulmonary arterial hypertension, Alport syndrome, non-alcoholic steatohepatitis, focal segmental glomerulosclerosis, Huntington's disease, Parkinson's disease, Alzheimer's disease, amyotrophic lateral sclerosis, liver cirrhosis, non-alcoholic fatty liver disease, hepatitis acute kidney injury, sepsis, chronic kidney disease, systemic lupus erythematosus nephritis, pulmonary emphysema, pulmonary fibrosis, chronic obstructive pulmonary disease, asthma, inflammatory lung disease, lymphocytic interstitial pneumonia, splenomegaly, type 1 diabetes, type 2 diabetes, diabetic nephropathy, diabetic retinopathy, diabetic cardiomyopathy, hyperglycaemia, arthritis, scleroderma, atopic dermatitis, lymphadenopathy, alopecia, hyperthyroidism, oesophageal achalasia, thrombocytopenia, neutropenia, autoimmune haemolytic anaemia, frontotemporal dementia, autism spectrum disorder, multiple sclerosis or Friedreich's ataxia.

22. The use according to statement 21, wherein the cancer is breast cancer.

23. The use according to statement 22, wherein the breast cancer is ER+ or HER2− metastatic breast cancer.

24. A complex according to statements 1 to 7 or 13, or a pharmaceutical composition according to claims 14 to 18, in combination with one or more additional therapeutic agents.

25. The combination according to statement 24, wherein the additional therapeutic agents comprise an aromatase inhibitor, tamoxifen, exemestane, fulvestrant, an oral SERD or a CDK4/6 inhibitor.

EXAMPLES

Particular embodiments of the invention are further described hereinafter, with reference to the accompanying drawings, in which.

Figure 23:
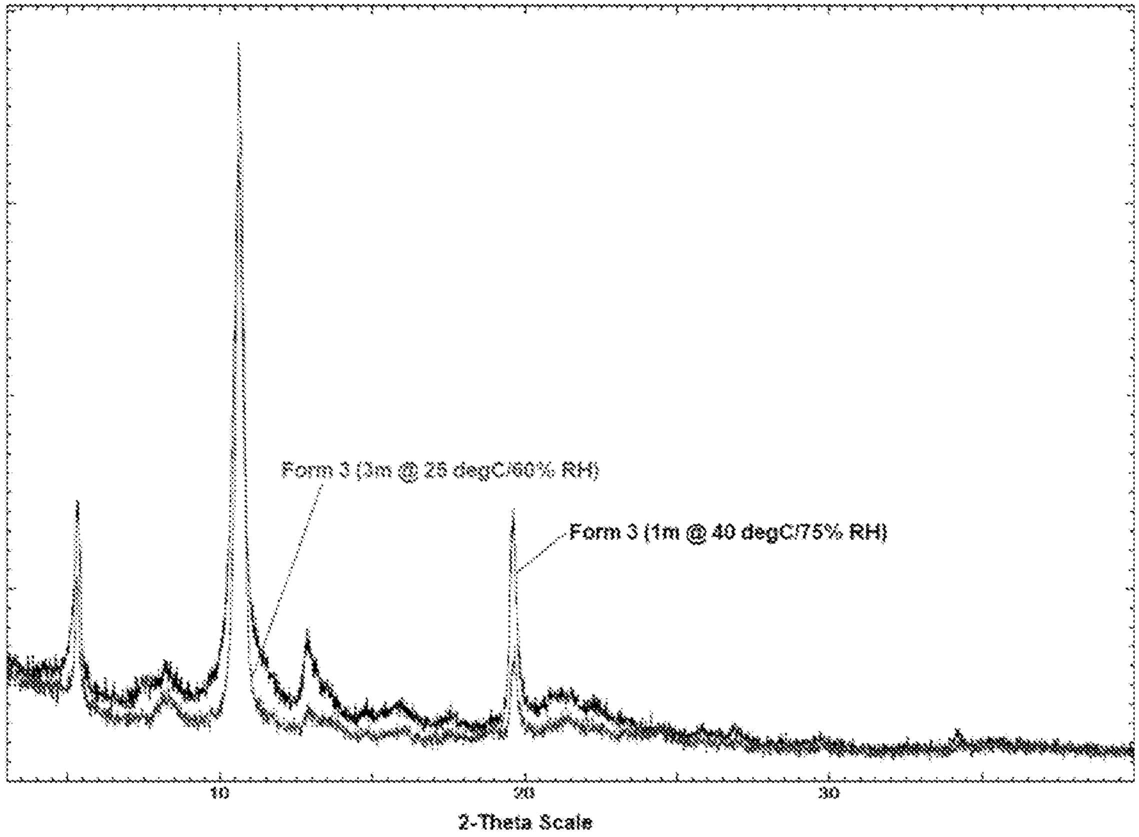

FIG. 23 shows an XRPD overlay in reflection mode of Form 3 (Example 5.3) after storage at 40° C. & 75% RH for 1 month (top) and 25° C. & 60% RH for 3 months (bottom).

The following abbreviations have been used in the Examples:

DMSO—dimethyl sulfoxide
eqv—molar equivalents
FaSSIF—Fasted State Simulated Intestinal Fluid
GVS—Gravimetric Vapour Sorption
HPLC—High Performance Liquid Chromatography
KF—Karl Fischer water analysis
NMR—Nuclear Magnetic Resonance
RH—Relative Humidity
RPM—Revolutions Per Minute
RRT—Relative Retention Time
TGA—Thermo Gravimetric Analysis
XRPD—X-Ray Powder Diffraction

INSTRUMENTS AND METHODOLOGY

XRPD

XRPD diffractograms were collected on a PANalytical Empyrean diffractometer using Cu Kα radiation (45 kV, 40 mA) in transmission geometry. A 0.5° sat, 4 mm mask and 0.04 rad Soller slits with a focusing mirror were used on the incident beam. A PIXcel$^{3D}$ detector, placed on the diffracted beam, was fitted with a receiving slit and 0.04 rad Soller slits. The software used for data collection was X'Pert Data Collector using X'Pert Operator Interface. The data were analysed and presented using Diffrac Plus EVA or HighScore Plus.

Samples were prepared and analysed in a metal 96 well-plate in transmission mode. X-ray transparent film was used between the metal sheets on the metal well-plate and powders (approximately 1-2 mg) were used as received. The scan mode for the metal plate used the gonio scan axis. The details of the standard screening data collection method are:

Angular range: 2.5 to 32.0° 2θ
Step size: 0.0130° 2θ
Collection time: 12.75 s/step (total collection time of 2.07 min).

Non-ambient conditions: XRPD diffractograms were collected on a PANalytical Empyrean diffractometer using Cu Kα radiation (45 kV, 40 mA) in reflection geometry. The instrument is fitted with an Anton Paar CHC plus$^+$ stage fitted with graphite/Kapton windows and equipped with air cooling coupled with a proUmid MHG32 Modular Humidity Generator or a low vacuum pump system using an Edwards RV3 pump. A programmable divergence slit (in automatic mode), with a 10 mm fixed incident beam mask, Ni filter and 0.04 rad Soller slits were used on the incident beam. A PIXcel$^{3D}$ detector, placed on the diffracted beam, was fitted with a programmable anti-scatter slit (in automatic mode) and 0.04 rad Soller slits. The software used for data collection was X'Pert Data Collector and the data analysed and presented using Diffrac Plus EVA or Highscore Plus.

For variable humidity (VH-XRPD) experiments the samples were prepared and analysed in an Anton Paar chromed low-profile sample holder with silicon wafer insert. The measurement parameters are as per the standard screening data collection method (detailed above). For all variable humidity XRPD experiments, a pattern was recorded every hour.

In some experiments, XRPD diffractograms were collected on a Panalytical X'pert Pro MPD X-Ray Diffractometer equipped with a Cu X-ray tube and a Pixcel detector system.

Further XRPD diffractograms were collected on a Bruker AXS D8 diffractometer using Cu Kα radiation (40 kV, 40 mA) and a θ-2θ goniometer fitted with a Ge monochromator in reflection geometry. The incident beam passes through a 2.0 mm divergence slit followed by a 0.2 mm anti-scatter slit and knife edge. The diffracted beam passes through an 8.0 mm receiving slit with 2.5° Soller slits followed by the Lynxeye Detector. The software used for data collection and analysis was Diffrac Plus XRD Commander and Diffrac Plus EVA respectively. Samples were run under ambient conditions as flat plate specimens using powder as received. The sample was prepared on a polished, zero-background (510) silicon wafer by gently pressing onto the flat surface or packed into a cut cavity. The sample was rotated in its own plane. The details of the standard data collection method are: Angular range: 2 to 42° 2θ; Step size: 0.05° 2θ; Collection time: 0.5 s/step (total collection time: 6.40 min).

NMR $^1$H NMR spectra were collected on a Bruker 400 MHz instrument equipped with an auto-sampler and controlled by a DRX400 console. Samples were prepared in DMSO-$d_6$ solvent. Automated experiments were acquired using ICON-NMR configuration within Topspin software, using standard Bruker-loaded experiments ($^1$H). Off-line analysis was performed using ACD Spectrus Processor.

TGA

TGA data were collected on a TA Instruments Discovery TGA, equipped with a 25-position auto-sampler. Typically, 5-10 mg of each sample was loaded onto a pre-tared aluminium DSC pan and heated at 10° C./min from ambient temperature to 350° C. A nitrogen purge at 25 ml/min was maintained over the sample. The instrument control software was TRIOS and the data were analysed using TRIOS or Universal Analysis.

GVS

Sorption isotherms were obtained using a SMS DVS Intrinsic moisture sorption analyser, controlled by DVS Intrinsic Control software. The sample temperature was maintained at 25° C. by the instrument controls. The humidity was controlled by mixing streams of dry and wet nitrogen, with a total flow rate of 200 ml/min. The relative humidity was measured by a calibrated Rotronic probe (dynamic range of 1.0-100% RH), located near the sample. The weight change, (mass relaxation) of the sample as a function of % RH was constantly monitored by a microbalance (accuracy±0.005 mg).

Typically, 5-30 mg of sample was placed in a tared mesh stainless steel basket under ambient conditions. The sample was loaded and unloaded at 40% RH and 25° C. (typical room conditions). A moisture sorption isotherm was performed as outlined below (2 scans per complete cycle). The standard isotherm was performed at 25° C. at 10% RH intervals over a 0-90% RH range. Typically, a double cycle (4 scans) was carried out. Data analysis was carried out within Microsoft Excel using the DVS Analysis Suite.

TABLE 1

| Parameter | Value |
|---|---|
| Adsorption-Scan 1 | 40-90 |
| Desorption, Adsorption-Scan 2 | 90-0, 0-40 |
| Intervals (% RH) | 10 |
| Number of Scans | 4 |
| Flow rate (ml/min) | 200 |
| Temperature (° C.) | 25 |
| Stability (° C./min) | 0.2 |
| Sorption Time (hours) | 6 hour time out |
| Number of cycles | 2 |

Water Determination by KF Titration

The water content of each sample was measured on a Metrohm 874 Oven Sample Processor at 150° C. with 851 Titrano Coulometer using Hydranal Coulomat AG oven reagent and nitrogen purge. Weighed solid samples were introduced into a sealed sample vial. Approximately 10 mg of sample was used per titration and duplicate determinations were made. An average of these results is presented unless otherwise stated. Data collection and analysis were performed using Tiamo software.

Example 1: Formation of a Complex of Sulforaphane and α-Cyclodextrin (Form 1)

To degassed α-cyclodextrin (15 g, 0.01 eqv) in water (30 mL) at room temperature was added 1-isothiocyanato-4-methylthiobutane (250 g, 1 eqv—see WO 2013/179057 for preparation of this precursor). The solution was cooled to below 2° C. and 31.5% aqueous $H_2O_2$ (176 g, 1.05 eqv) was added over 20 min so that the internal temp only increased to 2° C. during the addition. The reaction mixture was allowed to warm to room temperature while stirring overnight. Testing showed 2.6% starting material remaining, so the solution was cooled to below 2° C. and additional $H_2O_2$ was added until testing showed that less than 1% starting material remained. The solution was filtered through a Buchner funnel to remove solids. The filtrate was used without further processing.

α-cyclodextrin (1523 g, 1 eqv) was dissolved in boiling water (4 L) and cooled to 50° C. The sulforaphane filtrate was added slowly and the mixture was stirred at 50° C. for 1 h, then at room temperature for 24 h. The reaction mixture was then cooled and stirred at approximately 5° C. for 4 h. The resultant slurry was filtered through a cooled Buchner funnel in 1.5 L batches to keep the solution cold. The collected solids were dried under vacuum on the Buchner funnel overnight with a nitrogen stream over the cake. The solids were transferred to a 5 L round-bottomed Morton flask and dried under vacuum on the rotary evaporator with the water bath at 25° C. for 19 hours. A complex having a water content of 13.2% w/w by Karl-Fischer analysis was obtained (1479 g, batch ref. LS-13-0002-S-8002). The material had a purity by HPLC of 97.5%.

Figure 1:
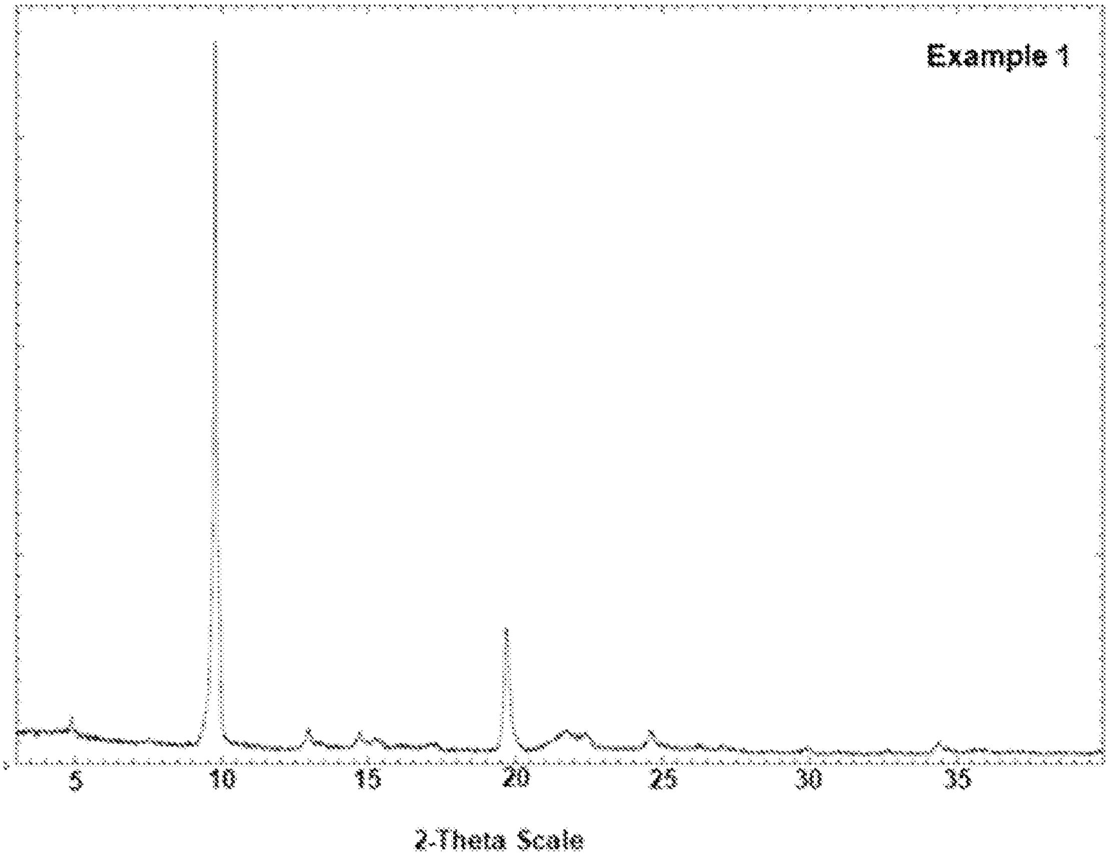
FIG. 1 shows XRPD analysis of Example 1 (Form 1) in reflection mode conducted on Panalytical X'pert instrument.
Figure 2:
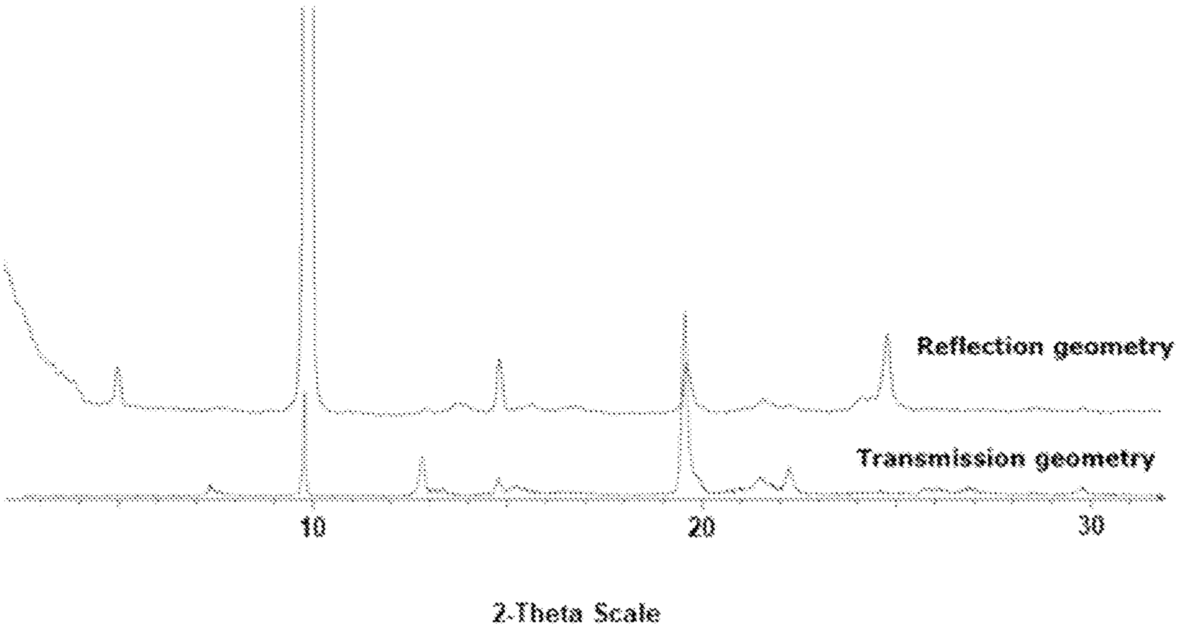
FIG. 2 shows an XRPD overlay of Form 1 in both reflection and transmission modes, conducted on Panalytical Empyrean instrument.

Analysis of Example 1 by XRPD (FIG. 1) indicated that it was Form 1. XRPD peak picking of Form 1 in reflection mode is summarised in Table 2.

TABLE 2

| Angle (°2θ) | Intensity % |
|---|---|
| 5.0 | 1.4 |
| 9.9 | 100.0 |
| 12.9 | 0.3 |
| 13.8 | 0.4 |
| 14.8 | 1.6 |
| 15.6 | 0.4 |
| 16.7 | 0.4 |
| 19.6 | 1.5 |
| 21.6 | 0.5 |
| 22.3 | 0.4 |
| 24.2 | 0.6 |
| 24.7 | 2.3 |
| 34.3 | 0.6 |
| 34.9 | 0.5 |
| 35.7 | 0.4 |

Example 1A: Formation of a Complex of Sulforaphane and α-Cyclodextrin According to Procedures in WO 2013/179057

To degassed α-cyclodextrin (30 g, 0.01 eqv) in water (1 L) at room temperature was added 1-isothiocyanate-4-rethylthiobutane (501 g, 1 eqv). The solution was cooled to 0° C. and degassed for 30 mins. To the suspension was added 35% aqueous $H_2O_2$ (305 ml, 1 eqv) slowly while maintaining the internal temp below 4° C. during the addition. The reaction mixture was stirred for 8 hr at ice bath temperature and was then allowed to warm to room temperature while stirring overnight. The solution was filtered to remove solids. The filtrate was refrigerated for 5 hr prior to use in the next step.

α-cyclodextrin (3015 g, 1 eqv) was dissolved in water (8 L) by heating up to 55° C. The solution was cooled down to room temperature and the sulforaphane filtrate from the previous step was added at once. The mixture was stirred at room temperature overnight. The reaction mixture was then cooled in an ice bath and stirred at that temperature for 3 hr. The precipitated solid was filtered through Buchner funnel and dried on the filter under vacuum overnight. The filter cake was transferred to a 10 L round-bottomed flask and dried under high vacuum at room temperature over the weekend to yield a white solid (2.74 kg, 76.9% yield; batch ref. 191PAL79). The solid had a water content of 11.3% w/w by Karl-Fischer analysis and a purity by HPLC of 98.5%. $^1$H-NMR analysis confirmed that Example 1A was a 1:1 sulforaphane:α-cyclodextrin complex.

Example 2: Formation of a Complex of Sulforaphane and α-Cyclodextrin (Form 2)

A sample of a Form 1 complex of sulforaphane and α-cyclodextrin (100 mg) was placed in a 4 mL vial and water (200 μl relative volumes) was added to form a slurry. The vial was capped and allowed to stand at room temperature overnight.

Figure 3:
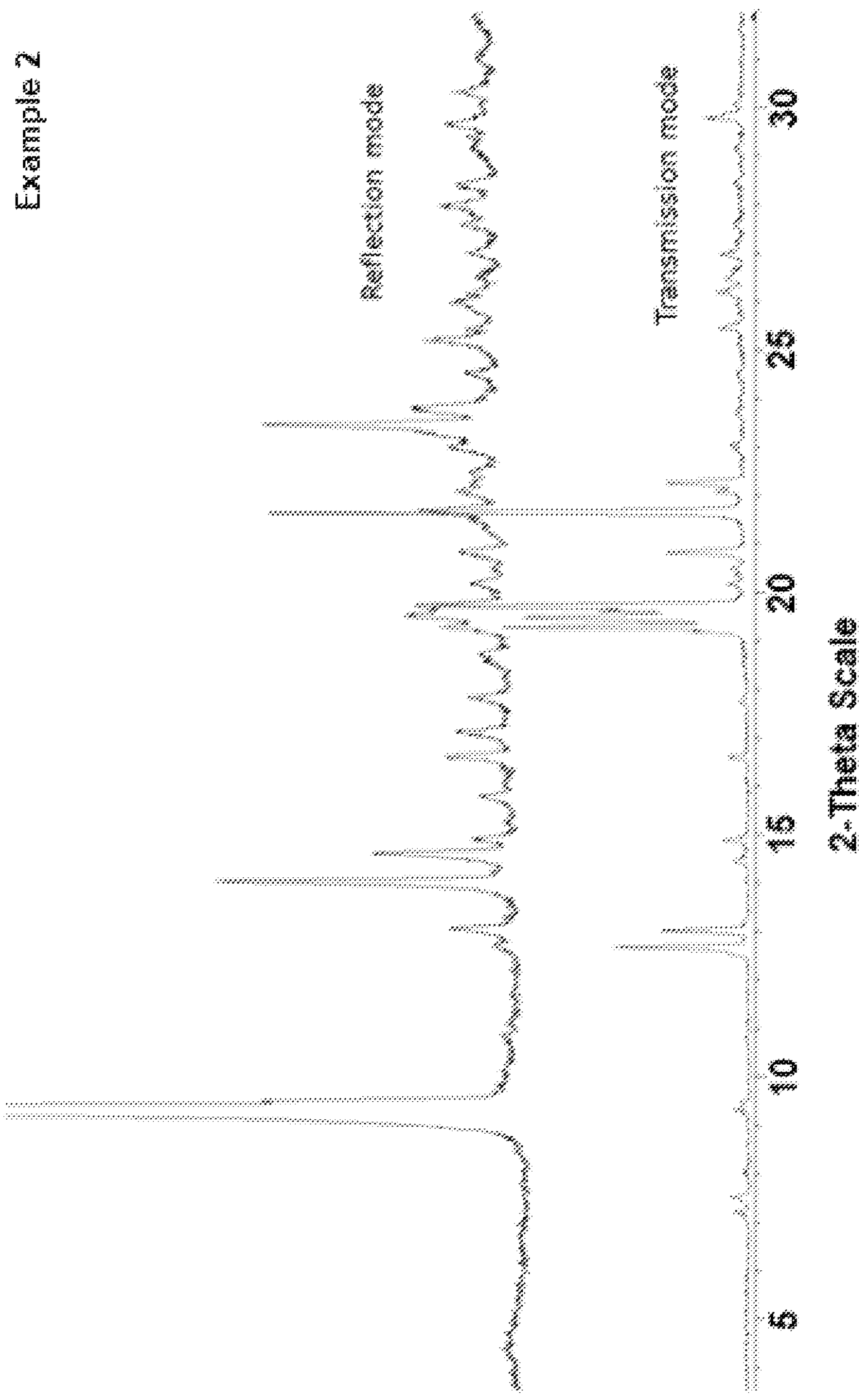
FIG. 3 shows an XRPD overlay of Example 2 (Form 2) in both reflection and transmission modes, conducted on Panalytical Empyrean instrument.

Analysis of an aliquot of the slurry of Example 2 by XRPD (FIG. 3) indicated that it was a different form, termed Form 2. XRPD peak picking of Form 2 in reflection mode is summarised in Table 3.

TABLE 3

| Angle (°2θ) | Intensity % |
|---|---|
| 9.5 | 100.0 |
| 14.2 | 14.7 |
| 14.8 | 1.1 |
| 18.9 | 2.3 |
| 19.7 | 1.3 |
| 23.6 | 14.7 |
| 23.9 | 4.2 |

XRPD peak picking of Form 2 in transmission mode is summarised in Table 4.

TABLE 4

| Angle (°2θ) | Intensity % |
|---|---|
| 7.2 | 5.8 |
| 7.5 | 5.3 |
| 8.9 | 5.6 |
| 9.1 | 9.7 |
| 9.3 | 57.1 |
| 12.7 | 29.4 |
| 13.0 | 30.8 |
| 14.0 | 4.6 |
| 14.4 | 8.0 |
| 14.9 | 6.1 |
| 16.6 | 8.6 |
| 18.6 | 5.2 |
| 19.3 | 48.3 |
| 19.5 | 50.7 |
| 19.7 | 90.5 |
| 20.2 | 6.5 |
| 20.8 | 21.9 |
| 21.7 | 100.0 |
| 22.1 | 7.9 |
| 22.3 | 17.5 |
| 22.9 | 4.8 |
| 23.4 | 3.9 |
| 23.7 | 5.7 |
| 25.5 | 9.5 |
| 26.2 | 11.5 |
| 26.5 | 6.7 |
| 27.0 | 7.3 |
| 29.2 | 5.1 |
| 29.8 | 13.6 |

Example 3: Small-Scale Formation of a Complex of Sulforaphane and α-cyclodextrin (Form 31)

A sample of sulforaphane:α-cyclodextrin Form 1 complex (300 mg) was weighed into a crystallisation dish, covered with tinfoil containing holes and placed in a vacuum oven at 40° C. for 24 hours, The sample was removed from the oven and left to cool at ambient temperature to leave a white solid (Batch Ref: DC-1771-19-02).

Figure 4:
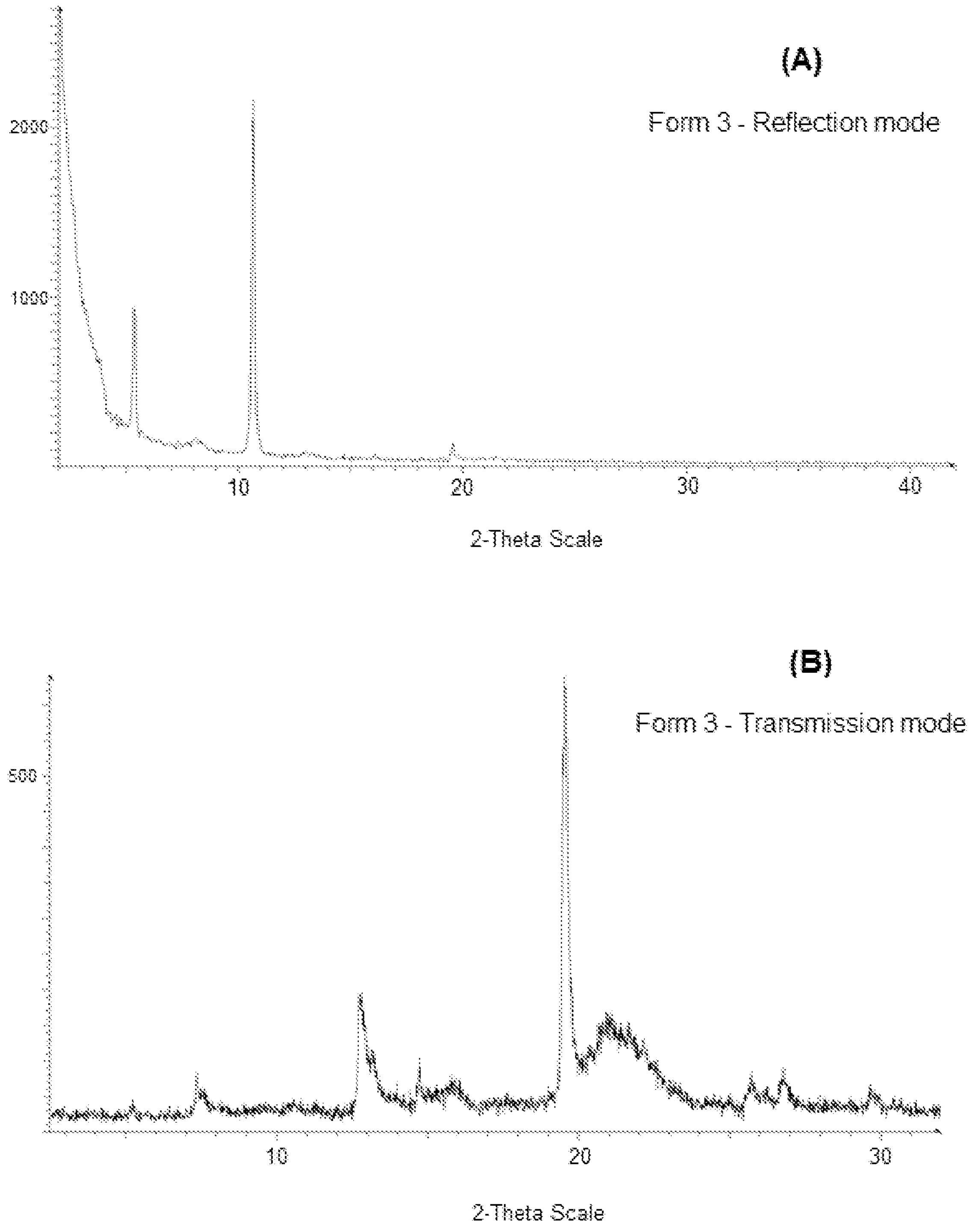
FIG. 4 shows an XRPD overlay of Example 3 (Form 3) in both reflection (A) and transmission (B) modes, conducted on Panalytical Empyrean instrument.

Analysis of Example 3 by XRPD in reflection mode (FIG. 4A) and transmission mode (FIG. 4B) indicated that it was a new form, referred to as Form 3. XRPD peak picking of Form 3 in reflection mode is summarised in Table 5.

TABLE 5

| Angle (°2-Theta) | Intensity % |
|---|---|
| 5.3 | 43.3 |
| 8.1 | 7.5 |
| 10.7 | 100 |
| 16.1 | 2.9 |
| 19.6 | 6.2 |

Figure 5:
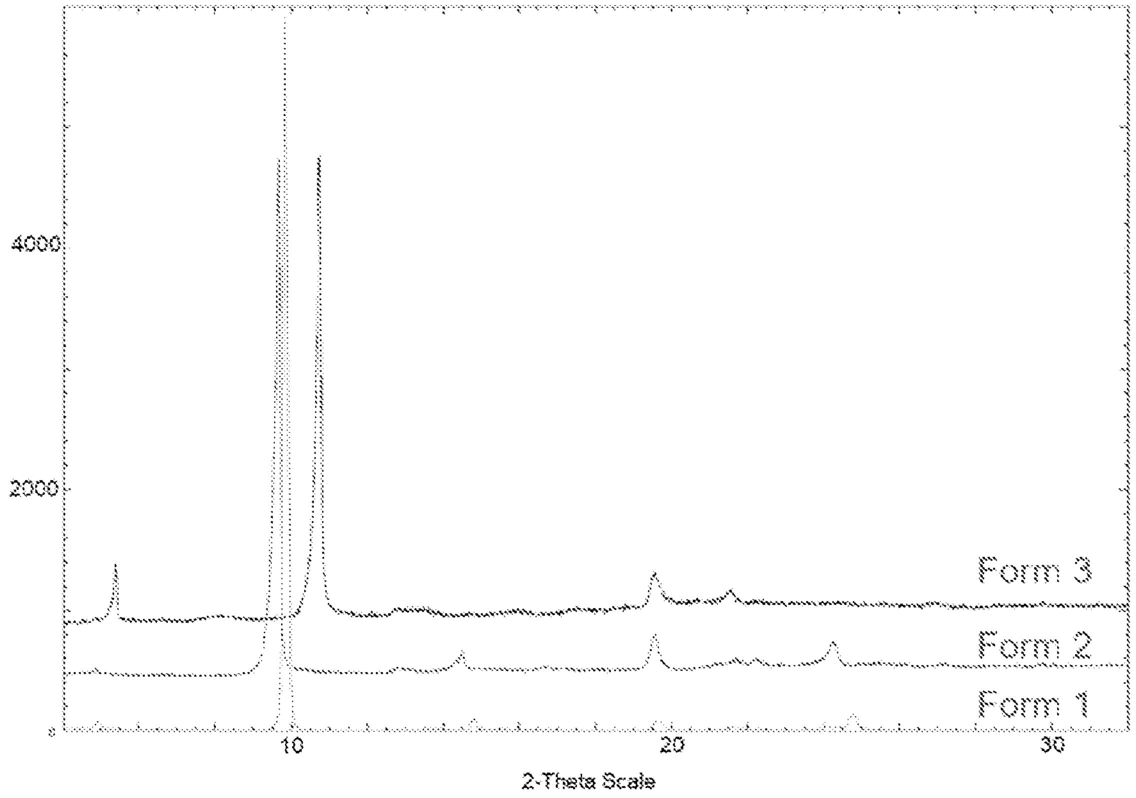
FIG. 5 shows an XRPD overlay of Forms 1, 2 and 3 run in reflection mode, conducted on Panalytical Empyrean instrument (Forms 2 and 3) and Bruker AXS D8 instrument (Form 1).

FIG. 5 shows an overlay of the XRPD scans for Forms 1, 2 and 3 run in reflection mode.

Figure 6:
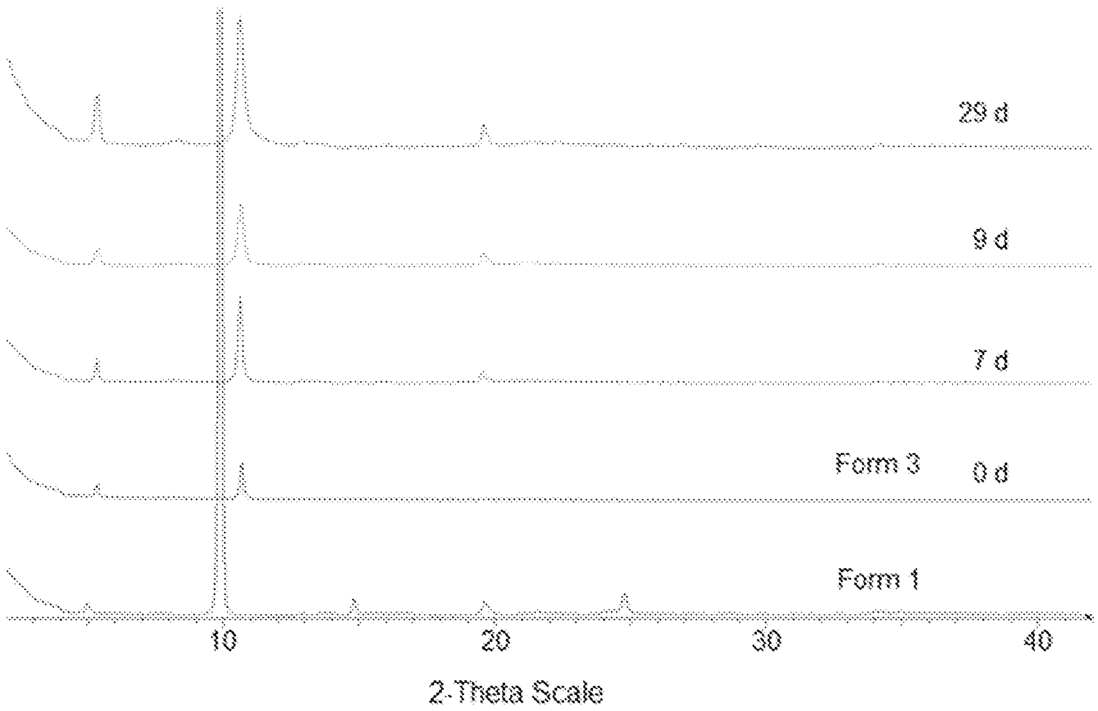
FIG. 6 shows an XRPD overlay of Form 1 and Example 3 (Form 3) in reflection mode after Example 3 had been exposed to ambient conditions for 0, 7, 9 and 29 days, conducted on Panalytical Empyrean instrument.

After removal from the vacuum oven (day 0), Example 3 was reanalysed by XRPD in reflection mode on days 7, 9 and 29. The subsequent analyses (FIG. 6) showed that up to 29 days after removing Example 3 from the drying oven it still existed as Form 3.

Figure 7:
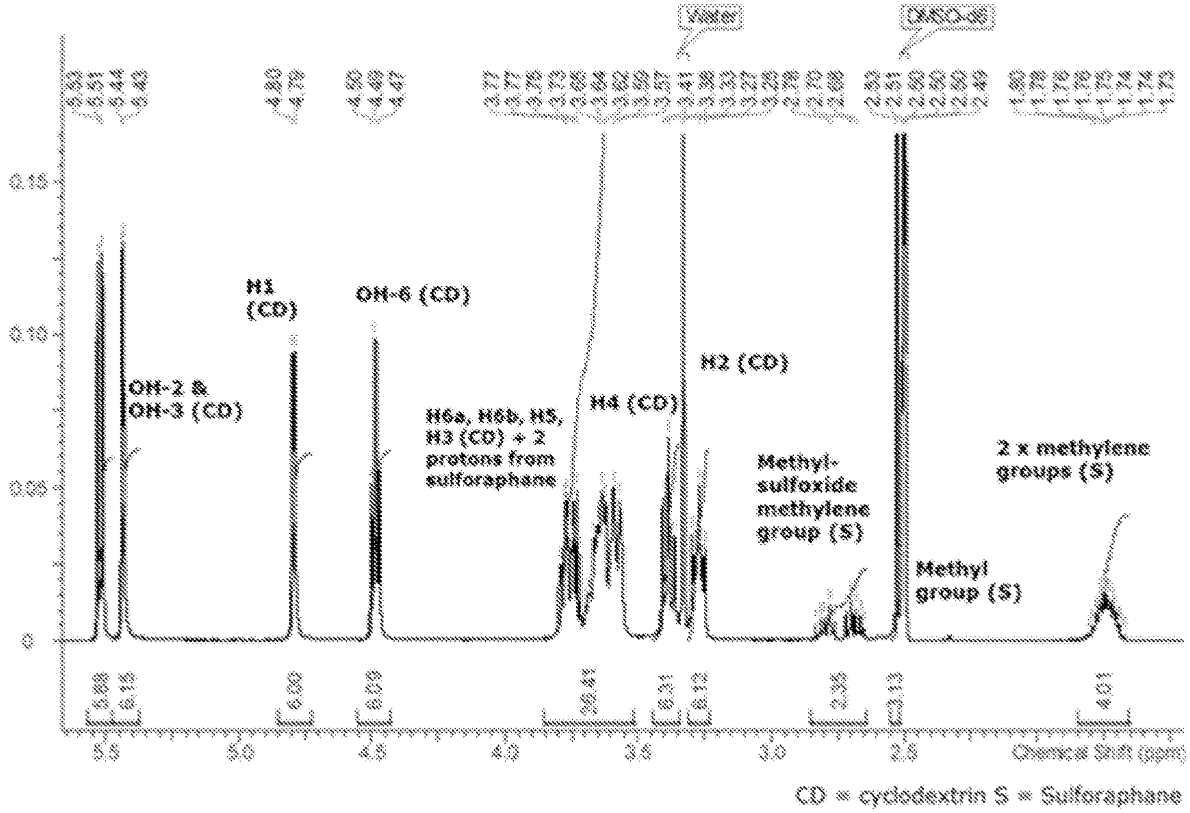
FIG. 7 shows a $^1$H-NMR spectrum of Example 3 run in DMSO-d6 at 400 MHz.

$^1$H-NMR (DMSO-$d_6$, 400 MHz) confirmed that Example 3 was a 1:1 sulforaphane:α-cyclodextrin complex with no evidence of decomposition (FIG. 7).

Example 3 was also analysed by TGA at days 1, 3, 7, 9, 15 and 20 after removal from the vacuum oven and exposure to ambient conditions, as described in Table 6.

TABLE 6

| Days exposed to ambient conditions | TGA mass loss (% wt) |
|---|---|
| 1 | 4.0* |
| 3 | 5.1 |
| 7 | 5.7 |
| 9 | 6.0 |
| 15 | 6.4 |
| 20 | 6.2 |

*average of two readings

As the TGA results indicate, after formation Form 3 gradually absorbed atmospheric moisture and stabilised to have a water content of approximately 6% wt, which corresponds to 3.5 to 4 water molecules per 1:1 sulforaphane: α-cyclodextrin complex.

Example 4: Formation of a Complex of Sulforaphane and α-Cyclodextrin (Intermediate Phase Between Form 1 and Form 3)

To degassed α-cyclodextrin (6 g, 0.01 eqv) in water (200 mL) at room temperature was added 1-isothiocyanato-4-methylthiobutane (100 g, 1 eqv). The solution was cooled to 0° C. and 35% aqueous $H_2O_2$ (60.2 mL, 1 eqv) was added slowly. The reaction mixture was allowed to gradually warm to room temperature while stirring overnight. The reaction mixture was filtered to remove solids. The filtrate was used without further processing.

α-cyclodextrin (603.1 g, 1 eqv) was dissolved in water (1.6 L) and added to the sulforaphane filtrate. The mixture was stirred at room temperature overnight. The reaction mixture was then cooled in an ice bath for 1 h. The resultant slurry was filtered through a Buchner funnel and dried under high vacuum overnight (408 g, batch ref. 191PAL68). A sample removed from the filter cake was found to have a purity by HPLC of 97.8% and a water content of 5.8% w/w by Karl-Fischer analysis. $^1$H NMR analysis ($D_2O$) confirmed that a 1:1 complex of sulforaphane:α-cyclodextrin had been formed.

Figure 8:
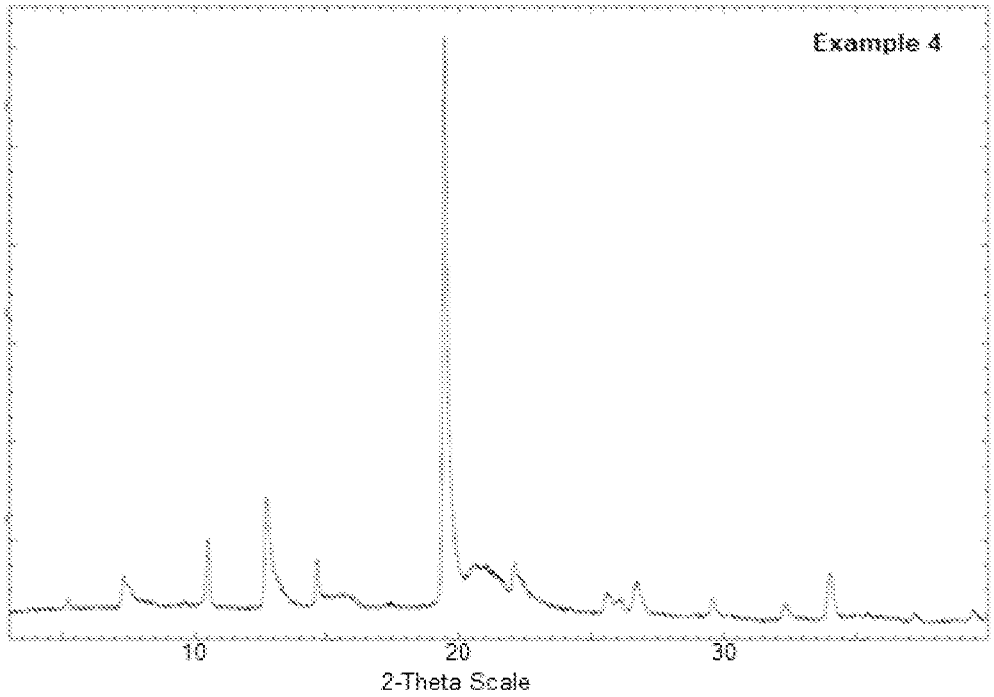
FIG. 8 shows (A) XRPD analysis of Example 4 in transmission mode conducted on Panalytical X'pert Pro instrument and (B) an XRPD overlay of Forms 1 and 3 (in both reflection and transmission modes) and Example 4 (transmission mode).
Figure 8:
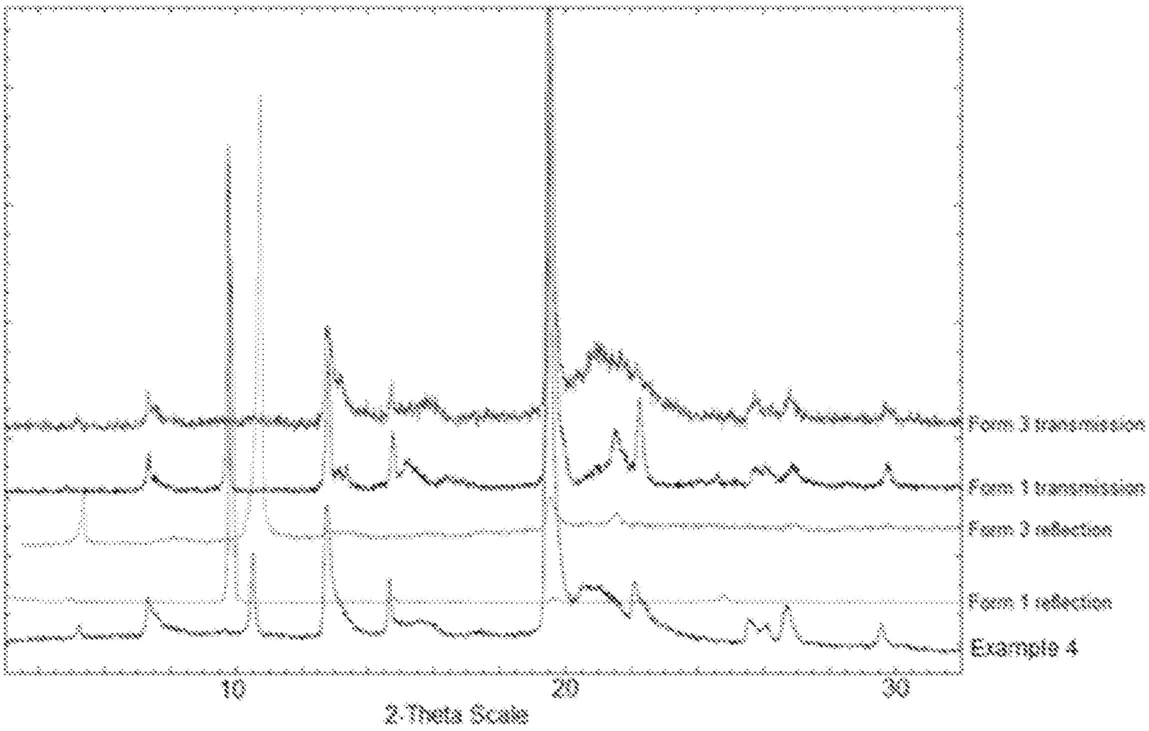

Analysis of Example 4 by XRPD (FIGS. 8A & 8B) indicated that it was an intermediate phase between Form 1 and Form 3 (main peak in reflection mode is at 10.49° 2θ).

Figure 9:
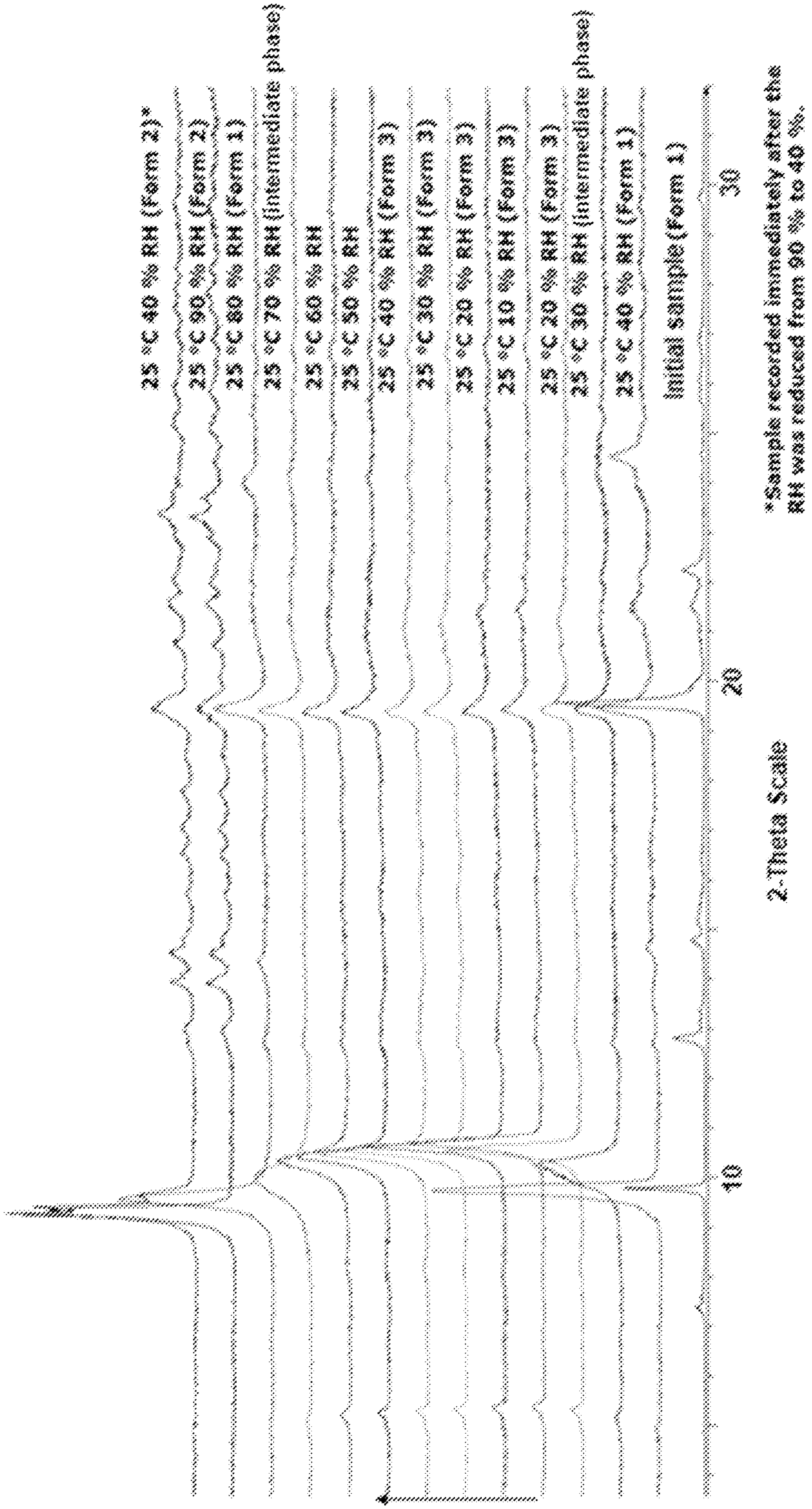
FIG. 9 shows a Variable Humidity-XRPD overlay in reflection mode of Form 1 carried out at 25° C.

The existence of such intermediate phases was also observed when a sample of Form 1 was exposed to variable humidity (VH) conditions at 25° C. and the solid state form was analysed by XRPD (FIG. 9). The Form 1 sample was loaded into the VH chamber, which was set to 40% RH and 25° C. and then the RH was decreased in 10% decrements to 10% RH followed by increasing the RH in 10% increments to 90% RH, while maintaining the temperature at 25° C. On reducing the RH, Form 1 converted to an intermediate phase at 30% RH, before changing to Form 3 at 20% RH. On increasing the RH the sample remained as Form 3, until at 70% RH an intermediate phase was again observed. The sample then quickly transitioned from Form 1 at 80% RH to Form 2 at 90% RH.

Example 5: Large-scale Formations of Form 3 Complex

Example 5.1

Form 1 complex was prepared analogously to Example 1 yielding a white solid having 98.8% purity by HPLC and 13.0% w/w water by KF.

A sample (10 g) of this material was placed into a crystallization dish and dried in a vacuum oven at either room temperature (Example 5.1.1) or 50° C. (Example 5.1.2) for 72 h.

Figure 10:
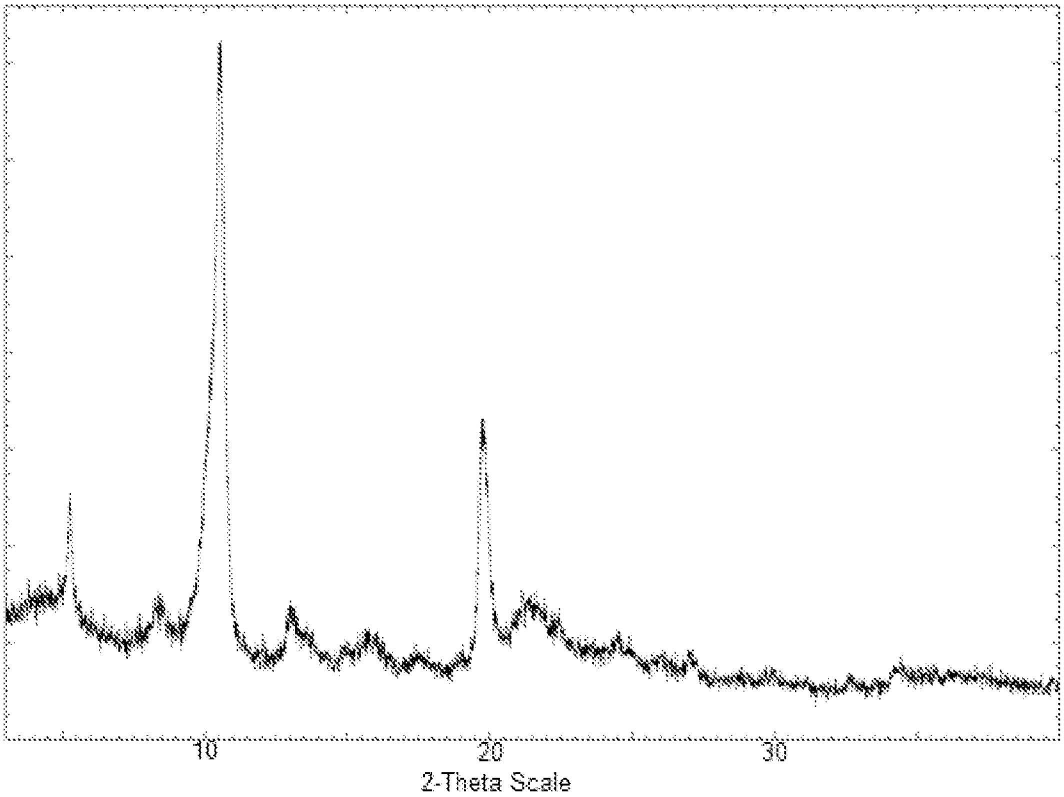
FIG. 10 shows XRPD analysis in reflection mode of Example 5.1.1, conducted on Panalytical X'pert instrument.

Example 5.1.1 (batch ref. A-19-0074) was found to contain 4.7% w/w water by KF and by XRPD (FIG. 10) was found to be a mixture of Form 1 and predominantly Form 3.

Figure 11:
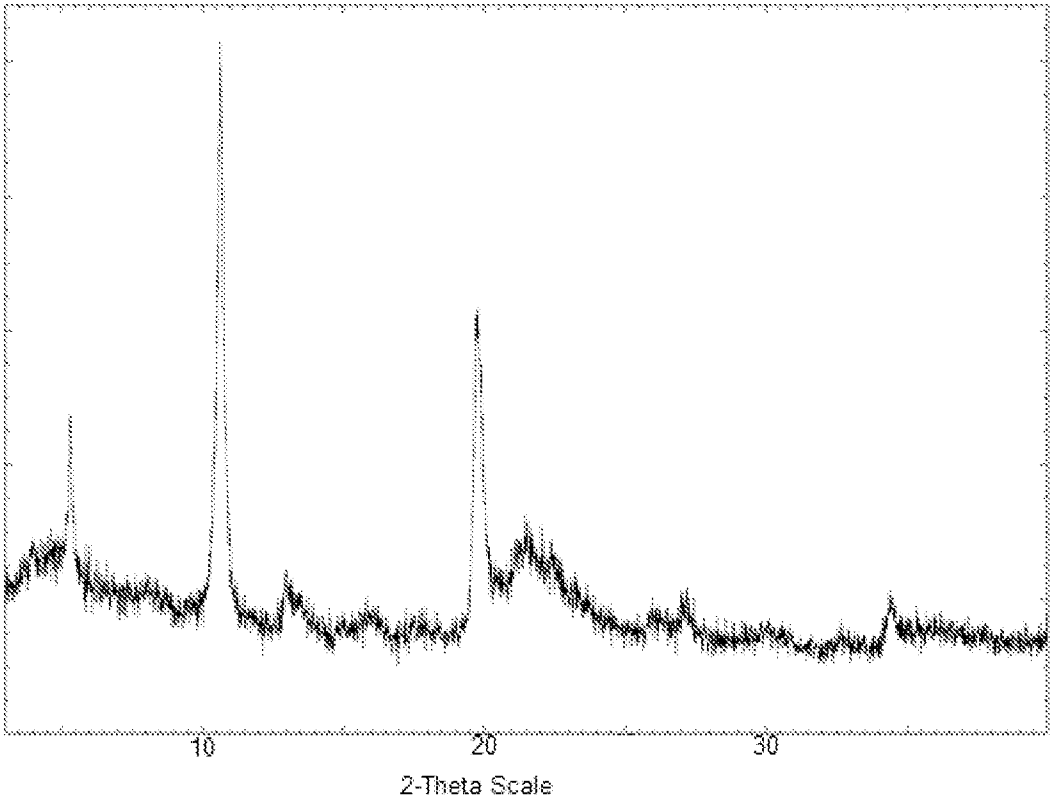
FIG. 11 shows XRPD analysis in reflection mode of Example 5.1.2, conducted on Panalytical X'pert instrument.

Example 5.1.2 (batch ref. A-19-0075) was found to contain 1.8% w/w water by KF and by XRPD (FIG. 11) was found to be predominantly Form 3 with very small amounts of an intermediate phase.

Example 5.2

Figure 12:
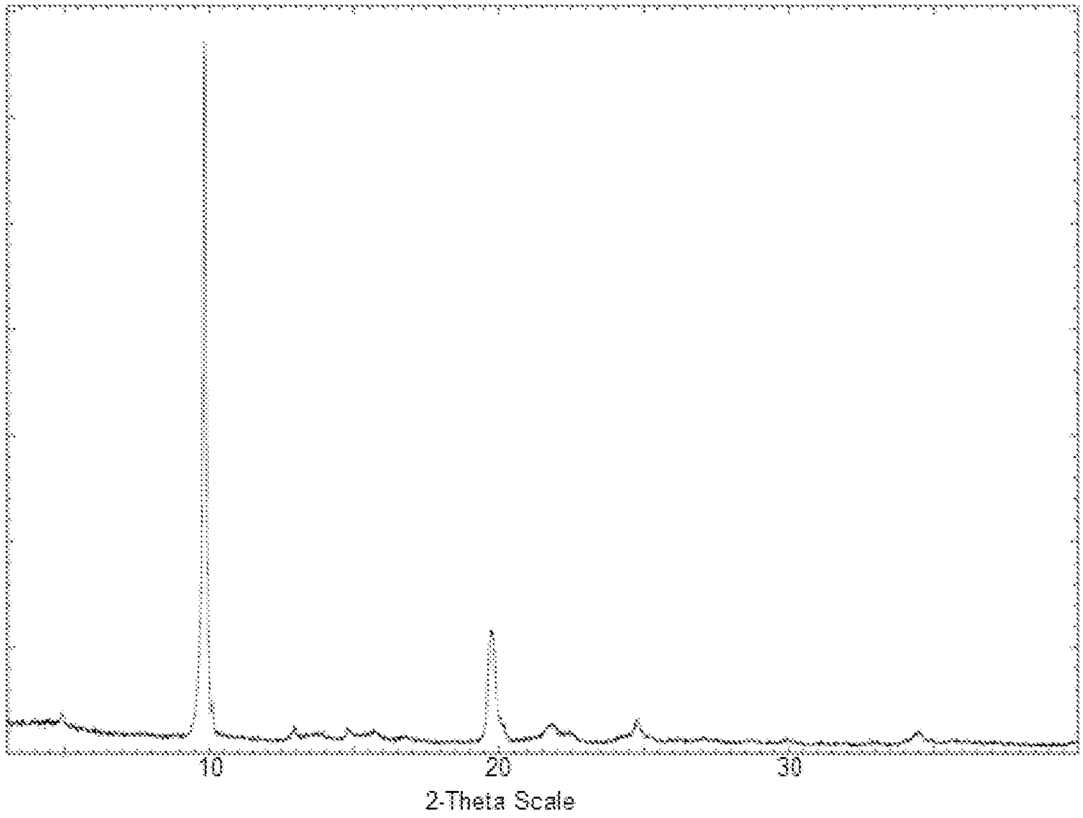
FIG. 12 shows XRPD analysis in reflection mode of Example 5.2, conducted on Panalytical X'pert instrument.

Sulforaphane:α-cyclodextrin complex was prepared on a 3 kg scale analogously to Example 1, except that after formation the precipitated complex was filtered off through a stainless steel funnel. The cake in the funnel was dried under vacuum with a $N_2$ bleed for 16 h and then under $N_2$ stream without vacuum for 72 h yielding a white solid (batch ref. 491PAL17; A-19-0098) containing 13.6% w/w water by KF. XRPD analysis of Example 5.2 (FIG. 12) indicated that it was a mixture of Form 1 and Form 2.

Figure 13:
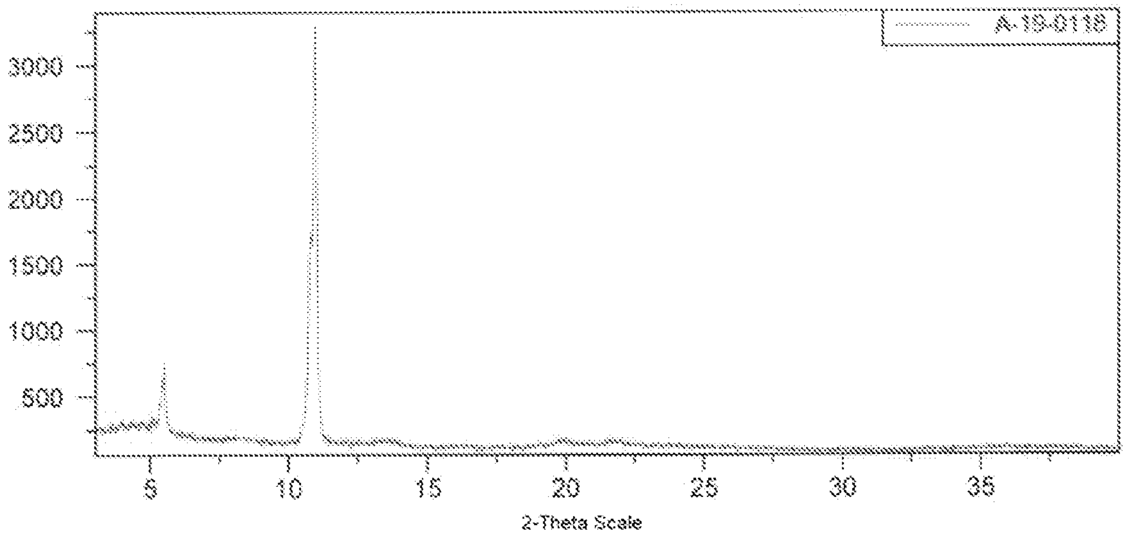
FIG. 13 shows XRPD analysis in reflection mode of Example 5.2.1, conducted on Panalytical X'pert instrument.

A sample (50 g) of this material was tray dried using a lyophiliser set up for 72 h under vacuum with the tray temperature set to 21° C. (Example 5.2.1). Example 5.2.1 (batch ref. A-19-0118) was found to contain 1.8% w/w water by KF and by XRPD (FIG. 13) was found to be predominantly Form 3.

Example 5.3

Sulforaphane:α-cyclodextrin complex was prepared on a 3 kg scale analogously to Example 1, except that after formation the precipitated complex was filtered off through a stainless steel funnel. The cake in the funnel was dried under vacuum with a $N_2$ bleed and limited agitation for 88 h to yield a white solid containing 8.5% w/w water by KF. XRPD analysis (FIG. 14A; A-19-0116) indicated that it was a mixture of Form 1 and Form 3.

Figure 14:
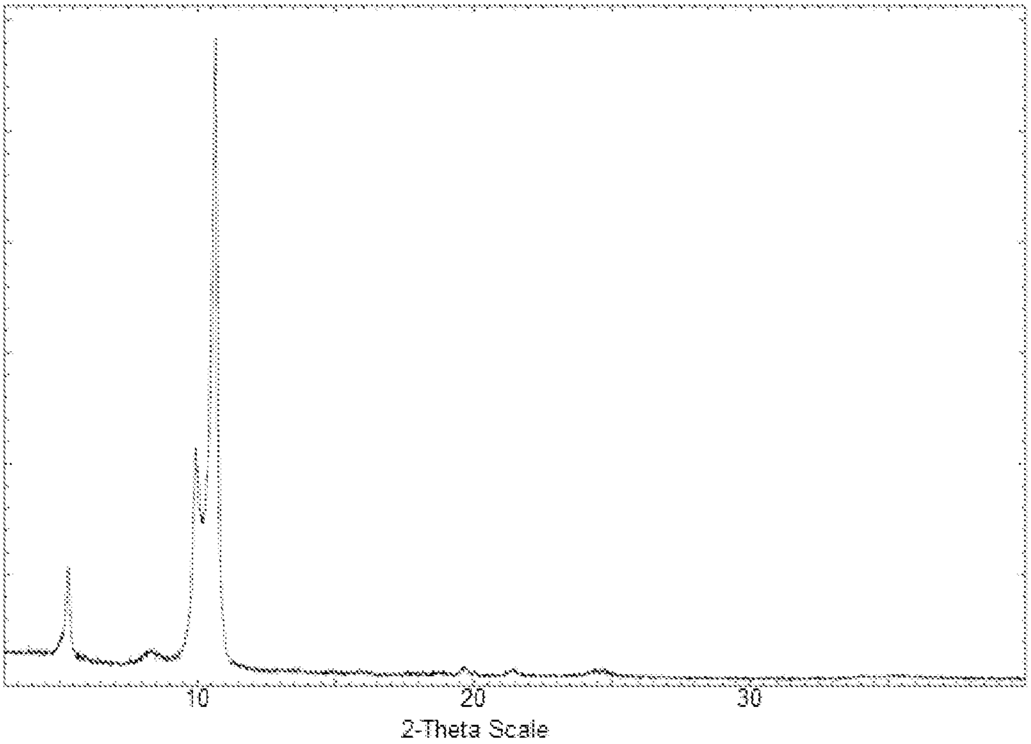
FIG. 14 shows XRPD analysis in reflection mode of Example 5.3, conducted on Panalytical X'pert instrument: (A) sample after 88 hr filter drying and (B) sample after subsequent tray drying.
Figure 14:
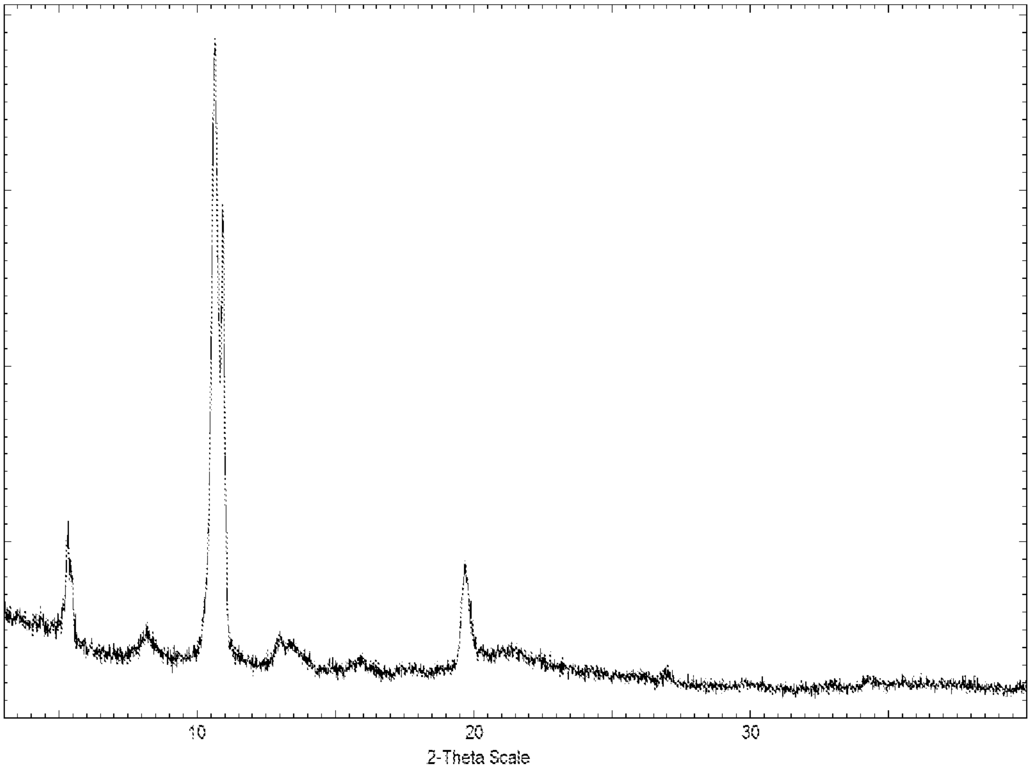

A 1.5 kg batch of this material was further dried in a tray in a drying oven at 21° C. and <1 torr (<1.3 mbar) for 72 hours to yield Example 5.3 (batch ref. 491PAL18) having 2.5% w/w water by KF and XRPD analysis (FIG. 14B; A-20-0220) showed a split peak indicating that it was predominantly Form 3 (10.70° 2θ), with a smaller amount of compressed Form 3 (10.91° 2θ).

Example 5.4

Figure 15:
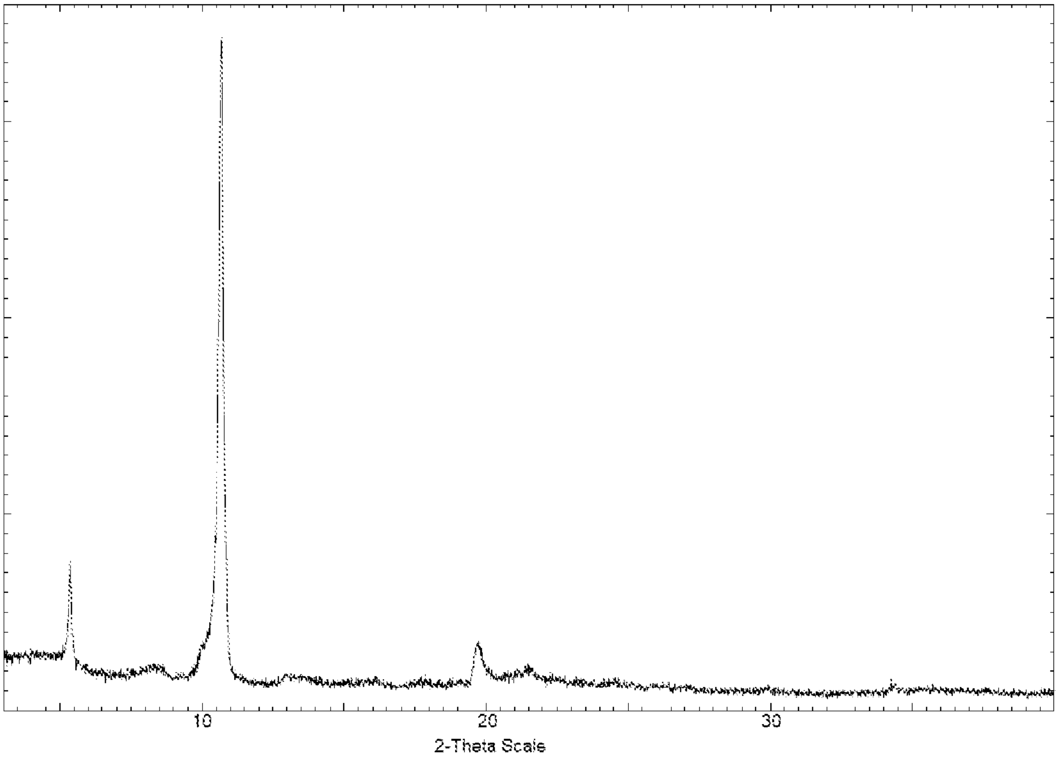
FIG. 15 shows XRPD analysis in reflection mode of Example 5.4, conducted on Panalytical X'pert instrument.

Sulforaphane:α-cyclodextrin complex was prepared on a 3 kg scale analogously to Example 1, except that after formation the precipitated complex was filtered off through a stainless steel funnel. The cake in the funnel was dried under vacuum with a $N_2$ bleed for 72 h and then under $N_2$ stream without vacuum for 6 days. The solid was then transferred to a 20 L round-bottomed flask and dried on a rotary evaporator at 25° C. without agitation for 4 days (batch ref. 491PAL22). Example 5.4 was found to be predominantly Form 3 by XRPD (FIG. 15) with some intermediate phase material.

Figure 16:
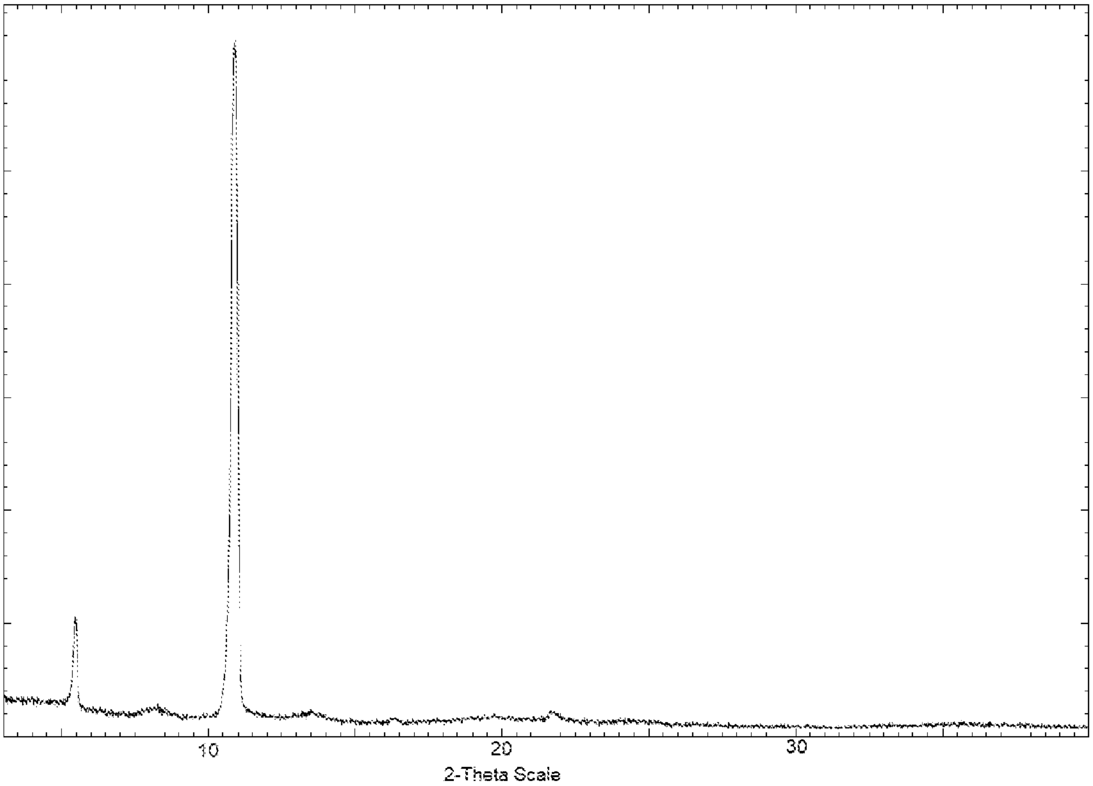
FIG. 16 shows XRPD analysis in reflection mode of Example 5.4.1, conducted on Panalytical X'pert instrument.

A sample (100 g) of this material was tray dried using a lyophiliser set up for 72 h under vacuum with the tray temperature set to 21° C. (Example 5.4.1). Example 5.4.1 (batch ref. A-19-0132) was found to contain 1.7% w/w water by KF and by XRPD (FIG. 16) was found to be predominantly Form 3.

Example 5B: Formation of Form 3 Complex—Filter Dryer Trials

Drying trials were carried out on water-wet sulforaphane: α-cyclodextrin complex isolated by filtration according to Example 1 with a water content by KF of 16±4% w/w. The trials were conducted on a scale of approximately 100 g using a laboratory scale Nutsche type filter dryer.

The filter dryer was fitted with temperature-controlled jacket, nitrogen supply, overhead agitation, condenser and vacuum connection to the condenser pipeline. The condenser was operated at 2° C. during the trials to prevent the vacuum lines from freezing with water vapour. The jacket was set to 15° C. prior to material being charged to the vessel. The wet complex was charged via the vessel manway, the vessel was sealed and agitation and vacuum (see Table 7 for agitation speeds and vacuum setpoints) were applied to the vessel. Once the desired vacuum had been achieved, the jacket temperature was increased to the desired set point (Table 7). A nitrogen bleed of ~0.45 L/min was applied to the vessel in the headspace above the charge material with the flowrate being monitored by an inline flowmeter. The drying was interrupted to take samples from the vessel to monitor the progress of the drying by KF and/or XRPD.

TABLE 7

| Trial | Jacket Temp (° C.) | Agitation (rpm) | Vacuum (mBar) | Drying Time (hr) | Recovery (%) | KF water content (% w/w) |
|---|---|---|---|---|---|---|
| 1 | 20 | 0/10 (mixed static/agitated) | 20 | 10 | 84 | 5.2 |
| 2 | 20 | 10-20 | 20 | 55 | 76 | 3.1 |
| 3 | 20 | 30 | 20 | 10 | 82 | 5.5 |
| 4 | 30 | 30 | 20 | 10 | 84 | 4.3 |
| 5 | 20 | 30 | 50-70 | 9 | 84 | 5.3 |
| 6 | 20 | 30 | 20 | 9 | 62 | 5.1 |

Trial 1 Summary

Figure 21:
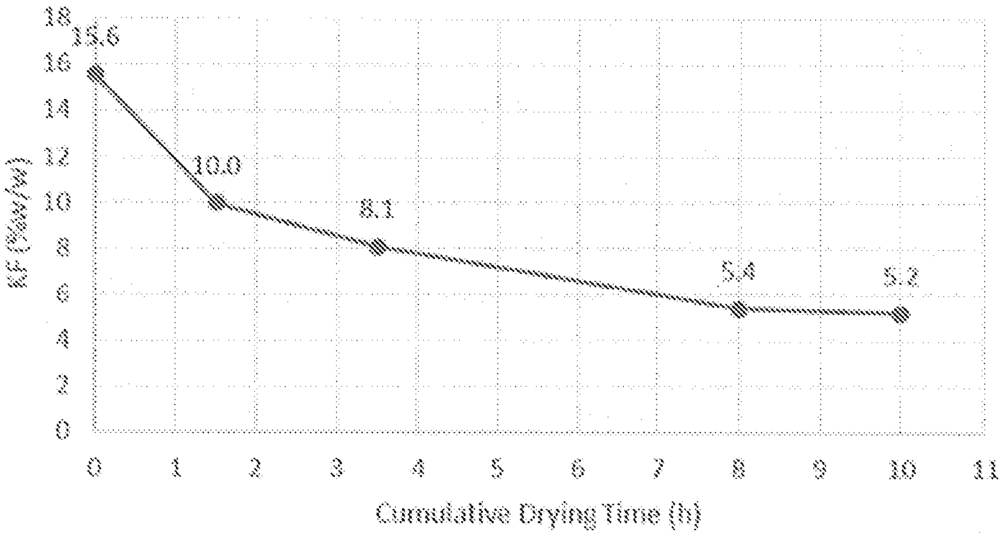
FIG. 21 shows the drying profile of sulforaphane:α-cyclodextrin complex with 15.6% w/w water content when dried at 20° C. and 20 mbar vacuum in a Nutsche-type filter dryer with mixed static and agitated (10 rpm) drying according to Example 5B (Trial 1).

Trial 1 was carried out with alternating periods of static (non-agitated) and agitated drying at 10 rpm. The vacuum achieved was 19-20 mbar. Four samples were taken over a cumulative drying period of 10 hours and tested for water content (see FIG. 21 and Table H). The drying profile shows that the material dried quickly initially, but that the speed of drying decreased after the water content went below ~6% w/w. More agglomerated material was observed after periods of static drying, however, these agglomerates were partially broken up during the periods of agitated drying. The final dried material showed an XRPD peak at 10.70° 2θ concordant with Form 3.

The water content and XRPD summary of the samples from Trial 1 at various time points during the drying are shown in Table 8.

TABLE 8

| Sample | Cumulative Drying Time (hr) | KF water content (% w/w) | Main XRPD peak (°2θ - reflection mode) | Solid State Form |
|---|---|---|---|---|
| 1 | 1.5 | 10.0 | 9.78 | 1 |
| 2 | 3.5 | 8.1 | 10.11 | intermediate |
| 3 | 8 | 5.4 | 10.70 | 3 |
| 4 | 10 | 5.2 | 10.70 | 3 |

Trial 2 Summary

Figure 22:
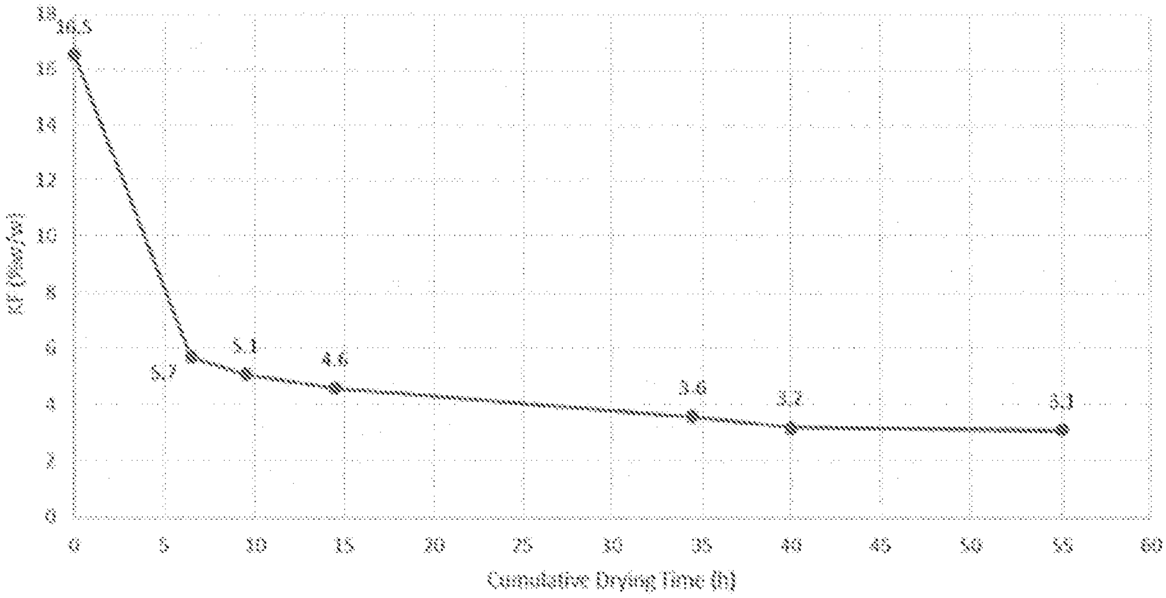
FIG. 22 shows the drying profile of sulforaphane: α-cyclodextrin complex with 16.5% w/w water content when dried at 20° C. and 20 mbar vacuum in a Nutsche-type filter dryer with constant agitated (10-20 rpm) drying according to Example 5B (Trial 2).

Trial 2 was carried out with constant agitated drying at 10-20 rpm. The vacuum achieved was 19-22 mbar. Six samples were taken over a cumulative drying period of 55 hours and tested for water content (see FIG. 22). The final water content was 3.1% w/w and the drying profile was consistent with Trial 1, showing that the material dried quickly initially, but that the speed of drying decreased after the water content went below ~6% w/w. Fewer agglomerates were observed compared to Trial 1 and the agglomerates decreased overtime. The final dried material showed an XRPD peak at 10.91° 2θ, suggesting that the final material at 3.1% w/w water was over-dried.

Trial 3 Summary

Trial 3 was carried out with constant agitated drying at 30 rpm. The vacuum achieved was 23-25 mbar. A drying target of 5.0-5.5% w/w water was set. The final water content was 5.5% w/w after 10 hours drying. Similar agglomerate levels to Trial 2 were seen. The final dried material showed an XRPD peak at 10.76° 2θ, concordant with Form 3. This trail showed that under these conditions, an agitated drying time of 10 hours was sufficient to obtain Form 3.

Trial 4 Summary

Trial 4 was carried out with constant agitated drying at 30 rpm, but with the temperature increased to 30° C. The vacuum achieved was 20-22 mbar. The final water content was 4.3% w/w after 10 hours drying. The final dried material showed an XRPD peak at 10.75° 2θ, concordant with Form 3. Similar agglomerate levels to Trial 2 were seen.

Trial 5 Summary

Trial 5 was carried out with constant agitated drying at 30 rpm and 20° C., but with a reduced vacuum of 50-70 mbar, The final water content was 5.3% w/w after 9 hours drying. The final dried material showed an XRPD peak at 10.71° 2θ, concordant with Form 3. Similar agglomerate levels to Trial 2 were seen.

A sample taken after 5 hours drying had a water content of 6.5% w/w and a main XRPD peak at 10.54° 2θ. This suggests that with the reduced vacuum, a drying time of at least 9 hours is required to yield material having the target 5.0-5.5% w/w water content. As this drying time is in line with trials 1 and 3 where a vacuum of 20 mbar was used, it was concluded that a reduction in vacuum strength from 20 mbar to 50-70 mbar can be tolerated without impacting drying efficiency.

Trial 6 Summary

Trial 6 was carried out using a different input material with a higher water content. Material from Trial 1 was slurried in 2.57 volumes of water at 5° C. for 3.5 hours in the filter dryer vessel. The slurry cake was blown down under a pressure of 0.5-0.75 barG to yield material with a 26.4% w/w water content. This material was blown down for a further 1 hour under nitrogen and then held at a jacket temperature of 0° C. overnight. This blown-down cake showed evidence of cracking and had a 29.5% w/w water content.

This material with a high water content of 25-30% w/w was then dried for 9 hours at 20° C. with a vacuum strength of 27-28 mbar. The cake in the filter dryer had a lower height than seen in previous trials and this contributed to poorer mixing. Initial agitation at 30 rpm showed mixing in the cake not dissimilar to that seen previously, however, within 15 minutes of starting agitation balling (golf ball-sized lumps) were observed. Agitation was stopped at this point and the direction of the agitator was turned from 'mixing' to 'smoothing' and the agitation was continued at 10 rpm to break up the balling. Once this had been achieved, the agitation direction was returned to 'mixing' and agitation was continued at 10 rpm. When no balling was observed after an hour, the agitation speed was increased to 30 rpm. No significant agglomeration was noted throughout the rest of the drying trial.

The final water content was 5.1% w/w after 9 hours drying. The final dried material showed an XRPD peak at 10.55° 2θ, concordant with Form 3. However, the overall XRPD pattern showed reduced intensity and a broadened peak thought to be associated with the presence of a mixed phase.

Filter Drying Trials—Assessment of Agglomeration

The degree of agglomeration of each of filter drying trials 2-6 was assessed by sieving a portion of each discharged dried material on a 2000 micron sieve and quantifying the oversize residue in relation to the input. The residual agglomerates were then analysed by XRPD in a similar manner to the trial samples with the modification that a zero-background silicon holder with cavity was used due to sample quantity. The results are summarised below in Table 9.

TABLE 9

| Trial | Agglomerates >2000 μm (% w/w) | Main XRPD peak (°2θ - reflection mode) | Solid State Form |
|---|---|---|---|
| 2 | 2.7 | 10.48 | intermediate |
| 3 | 2.5 | 10.55 | 3 |
| 4 | 3.9 | 10.61 | 3 |
| 5 | 3.3 | 10.54 | 3 |
| 6 | 23.1 | 10.47 | intermediate |

It can be seen that while the dried samples typically contained <5% w/w of agglomerates having a particle size greater than 2000 μm, the material obtained from trial 6 had a much higher level of agglomerates at 23.1% w/w. It can also be seen from the XRFD main peak values in Table I, that in the agglomerated material the conversion to Form 3 was less complete than in the bulk fine material.

Filter Drying Trials—Conclusions

The optimal drying conditions comprise agitated drying (preferably continuous agitated drying) in order to decrease the drying time and agglomeration and to ensure Form 3 can be reproducibly obtained.

A suitable nitrogen bleed and a vacuum of at least 70 mbar in combination with the agitated drying allow efficient drying to Form 3 within time frames of less than 10 hours.

A drying target of 5.0-5.5% w/w water was appropriate to yield Form 3 material (main XRFD peak at 10.7±0.2° 2θ in reflection mode).

It is not necessary to carry out the agitated drying at temperatures above 20° C. although temperatures up to 30° C. may be tolerated with minimal degradation of the sulforaphane:α-cyclodextrin complex.

The drying efficiency and dried material physical properties are negatively impacted by using an input material with too high a water content (greater than approximately 25% w/w water), thus requiring additional non-agitated drying steps.

Example 6: Testing of Form 3

Aqueous Manipulation

Figure 17:
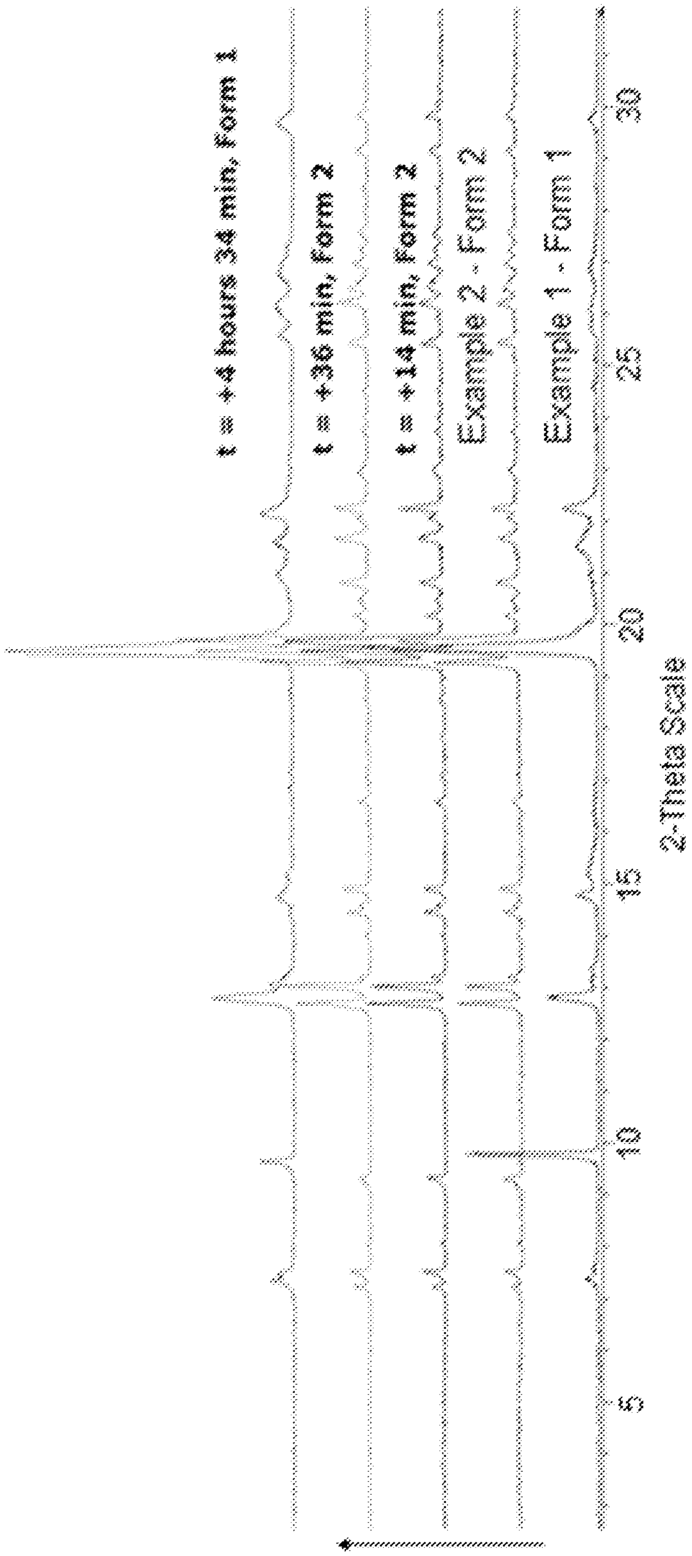
FIG. 17 shows an XRPD overlay of Form 1, Form 2 and a sample of a slurry of Example 4 (Form 3) in water run in reflection mode, at various timepoints after removal of the sample from the slurry, conducted on Panalytical Empyrean instrument.

Example 3—Form 3 (100 mg) was placed in a 4 ml vial, to which $H_2O$ (200 μl, 2 volumes) was added. The sample was capped and left at ambient temperature overnight. A spatula fill of the slurry was placed in a well and analysed by XRPD in transmission mode. The XRPD analysis was repeated every 5 minutes for 36 minutes on the same sample in the well. An XRPD was recorded 4 hours later too. The XRPDs are shown in FIG. 17. Form 3 converted to Form 2, when slurried in water, as seen by the XRPD patterns recorded after 14 and 36 mins. After having been left the 4 further hours at ambient conditions, the sample had converted from Form 2 to Form 1.

Exposure to Varying Humidity Levels

GVS

Figure 18:
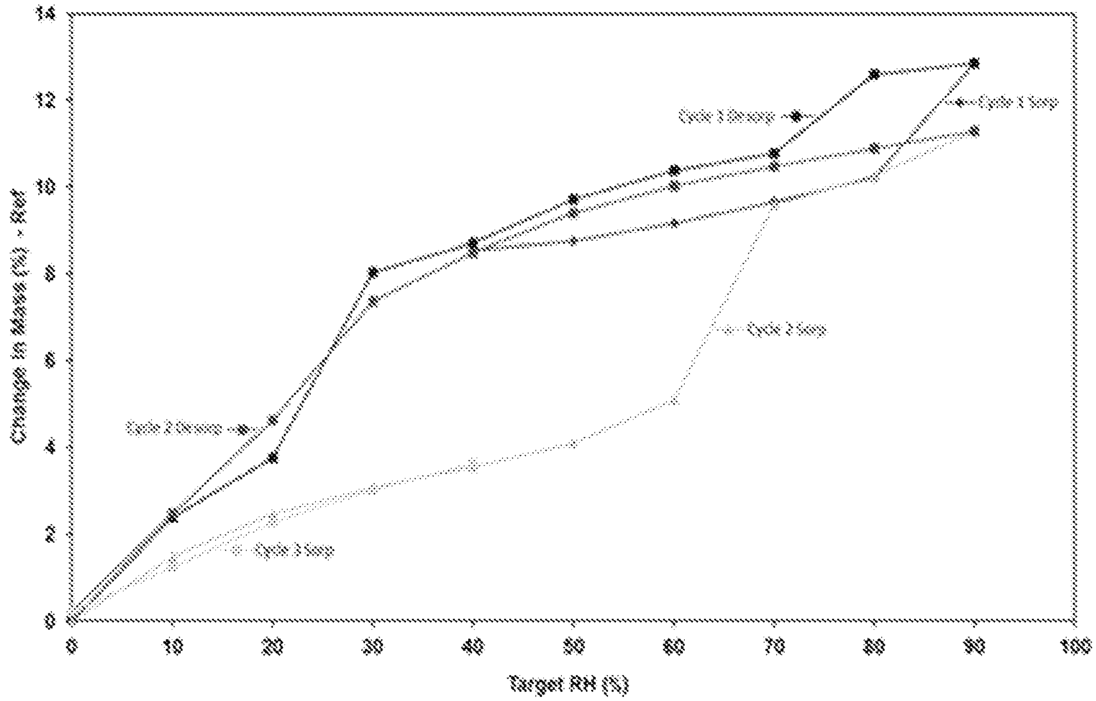
FIG. 18 shows GVS Isotherm plots of (A) Example 1 (Form 1) and (B) Example 4 (Form 3) with multiple sorption/desorption cycles.
Figure 18:
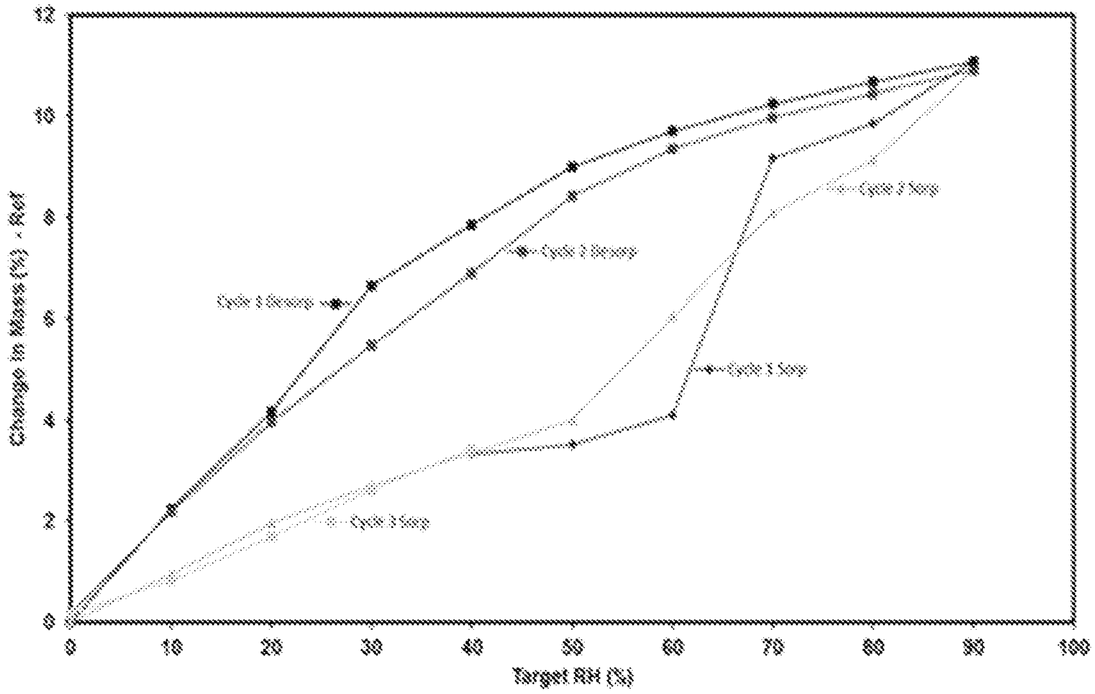

Samples of Example 1 (Form 1) and Example 3 (Form 3) were analysed for their sorption-desorption isotherms by GVS. FIG. 18A shows the GVS data for the Form 1 sample. The sample contained approximately 8% w/w water at the starting conditions of 40% RH and 25° C. As the RH was increased to 90% the sample took up an additional 4-5% w/w of water to 12.9% w/w total water content. Significant hysteresis existed between 70% and 30% RH. After the first sorption/desorption cycle, Form 1 had converted to Form 3 as confirmed by XRPD. Therefore, the second sorption profile seen in FIG. 18A is that of Form 3. FIG. 18B shows the GVS data for the Form 3 sample. The sample contained approximately 3-4% w/w water at the starting conditions of 40% RH and 25° C. As the RH was increased to 90% the sample took up an additional 7-8% w/w of water to 11.1% w/w total water content. A significant uptake of moisture occurred in the first sorption cycle between 60 and 70% RH equivalent to approximately 5% w/w. XRPD analysis confirmed that post-GVS the crystalline complex remains as Form 3.

These results demonstrate that Form 3 allows better control over the water content than Form 1. The GVS data show that between 0% and 60% RH Form 3 only takes up about 4% w/w water, whereas at 60% RH Form 1 will take up 8-9% w/w water.

VH-XRPD

Figure 19:
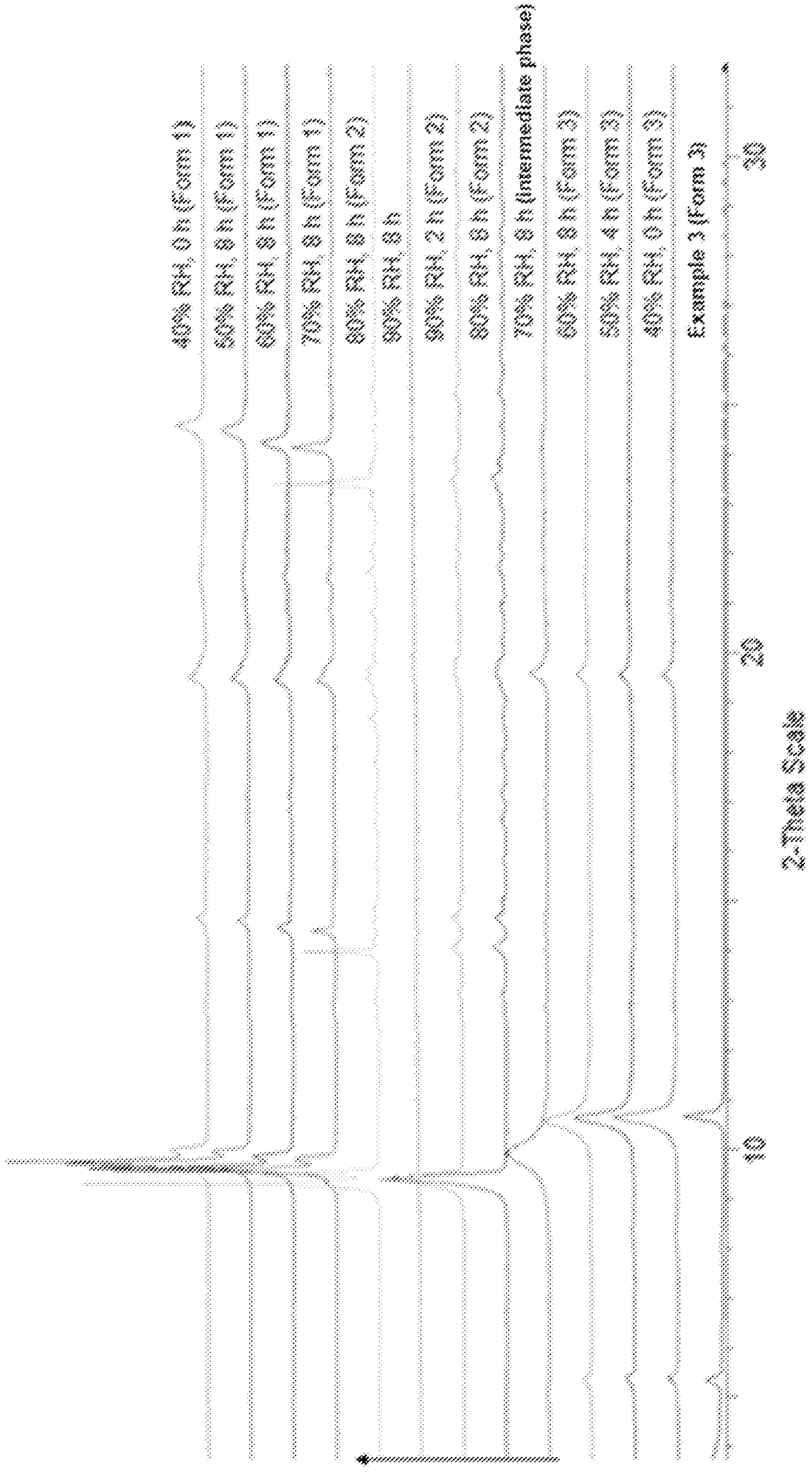
FIG. 19 shows a Variable Humidity-XRPD overlay in reflection mode of Example 4 (Form 3) carried out at 25° C.

A variable humidity (VH) XRPD experiment was performed to examine how Form 3 exists under different RH conditions. The VH-XRPD humidity profile for a sample of Example 3 (Form 3) is shown in FIG. 19. The sample was loaded into the VH chamber, which was set to 40% RH and 25° C. and then the RH was raised in 10% increments up to 90% RH wherein the RH was held at each increment for up to eight hours, before the RH was incrementally decreased to 40%, while maintaining the temperature at 25° C. Up to a RH of 60% Form 3 is maintained, however, after increasing it to 70% an intermediate phase is formed, which becomes Form 2 at 80% RH. The sample was stable as Form 2 for 8 hours at 80% RH. At 90% RH Form 2 existed for 2 hours before the sample deliquesced in the humidity chamber. After dropping the VH to 80% RH, Form 2 returned as a highly crystalline material. At 70% RH, Form 2 converted to Form 1 which persisted until the sample was removed from the humidity chamber at 40% RH.

The VH-XRPD experiment shows that Form 3 is stable over a wide RH range. From 0% to 60% RH Form 3 is stable at 25° C. It is not until the RH reaches 70% that Form 3 starts to convert to a different form. Therefore. Form 3 offers advantages over Form 1 in terms of improved handling over a wider RH range and better control of the crystalline complex form during storage. Table 10 summarises the three forms of crystalline 1:1 sulforaphane:α-cyclodextrin complex identified and their stability at 25° C.:

TABLE 10

| Form | Typical water content (% w/w) | Main XRPD peak (°2θ - reflection mode) | Stability at 25° C. |
|---|---|---|---|
| Form 1 | 8% to 15% | 9.8 ± 0.2 | Between 40 and 60% RH |
| Form 2 | 13% to 20% | 9.5 ± 0.2 | Above 80% RH |
| Form 3 | 3% to 7% | 10.7 ± 0.2 | Between 0 and 60% RH |

Figure 20:
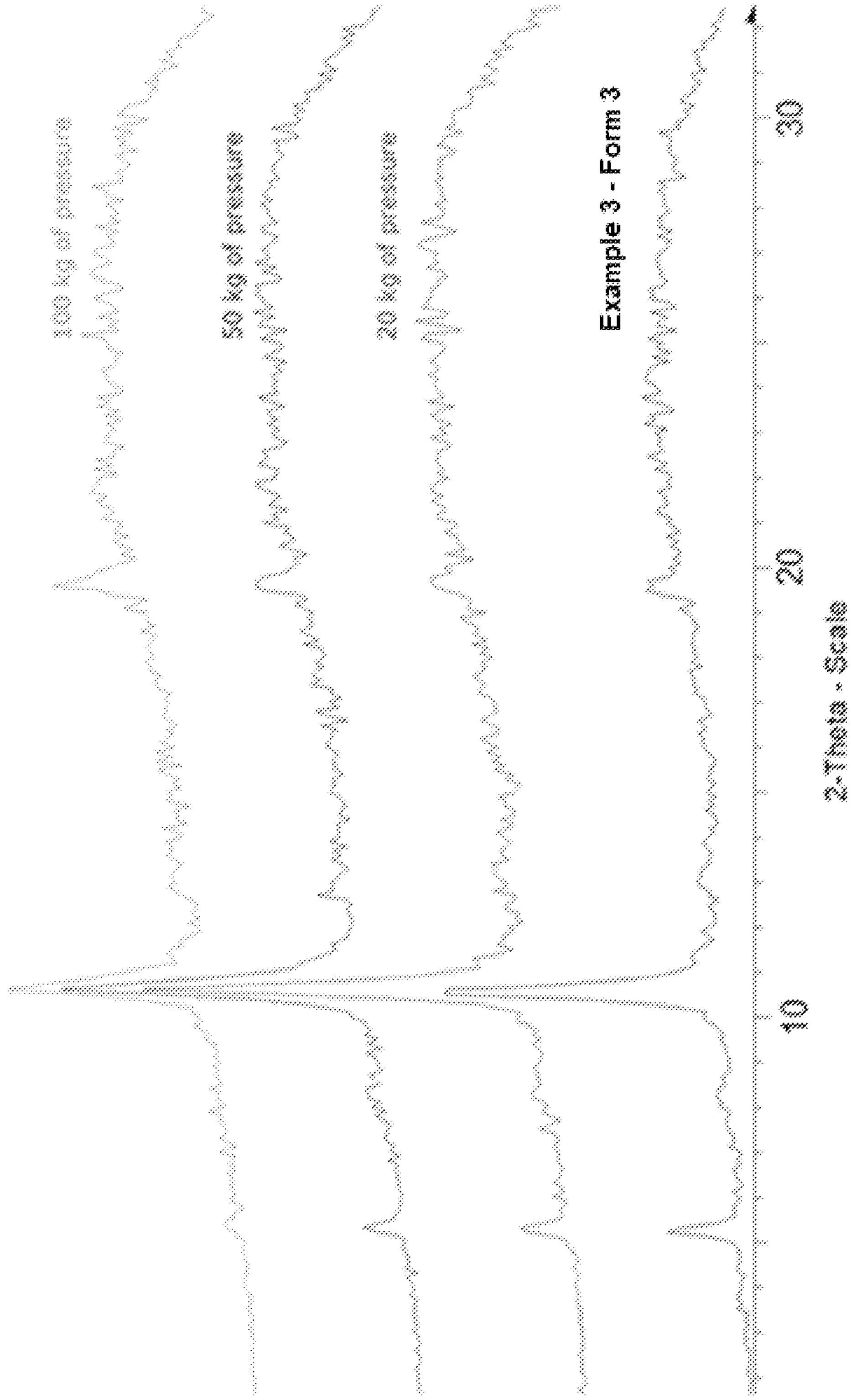
FIG. 20 shows an XRPD overlay in reflection mode of Example 4 (Form 3) discs after compression with 20 kg, 50 kg and 100 kg.

Compression Testing 15 mg samples of Example 3 (Form 3) were compressed into 3 mm recess discs under 20 kg, 50 kg and 100 kg of pressure for 2 minutes each. No decomposition of the compressed samples was evident by $^1$H-NMR. FIG. 20 shows the XRPD overlays for the compressed samples confirming that the samples still existed as Form 3, although there was a small loss in intensity of the major Bragg peaks.

Compaction Testing

Samples of Form 1 and Form 3 were subjected to Heckel analysis to determine the yield pressure of the material upon compression under controlled conditions. A known weight of material was compressed within a 10 mm diameter die with flat faced punches moving at a set speed. The die was lubricated with magnesium stearate in acetone. The force on the punch was accurately measured at frequent intervals whilst the displacement of the punches was used to calculate the volume of the powder. The yield pressure was calculated at slow (0.1 mm/s) and fast (300 mm/s) punch speeds to assess the time dependant component to deformation of the material. The true density of the material was determined by Helium Pycnometry (Micromeritics AccuPyc II 1340) using a purge pressure and run fill pressure of 19.5 psig and an equilibration rate of 0.02 psig. Testing was performed in duplicate. Temperature and humidity were monitored at intervals during the testing.

The data were analysed by the Compaction Analysis software programme to generate values for yield pressure (Py) using the Heckel equation:

$$\ln(1/1-D)=kP+A$$

where D=the relative density of the compact; P=Pressure applied; and K=Gradient of the line in the linear region [Heckel, *Trans. Metall. Soc. AIME* 221 (1961)1001-1008].

Strain Rate Sensitivity (SRS) can be calculated to determine whether the deformation characteristics of the material change with the rate of applied force. The yield pressure at high speed compression is compared to that at slow speed using the following equation [Roberts and Roe, *Chem. Eng. Sci.* 42(1987) p. 903].

$$\%\ SRS=100\times[(Py\ Fast-Py\ Slow)/Py\ Slow]$$

Loss on drying was carried out on the samples at the start and at the end of compression testing to monitor for moisture absorption during testing. A sample size of 2.0 g±0.2 g was spread onto an aluminium tray and dried until stable at 105° C. using a Mettler HB43-S Halogen moisture balance.

The results of the compaction testing are shown in Table 11.

TABLE 11

| Property | Form 1 | Form 3 |
|---|---|---|
| True Density | 1.4586 g/cm$^3$ | 1.4562 g/cm$^3$ |
| Yield pressure slow | 76.3 (±1.05) MPa | 108.7 (±2.90) MPa |
| Yield pressure fast | 88.9 (±2.32) MPa | 140.4 (±3.65) MPa |
| Strain rate sensitivity | ±16.5% | ±29.1% |
| Loss on Drying - start | 4.07% w/w | 1.99% w/w |
| Loss on Drying - end | 4.25% w/w | 1.13% w/w |

The compaction results indicate that Form 1 is classified as soft ductile, whereas Form 3 is classified as moderately hard brittle/ductile.

The yield pressure for Form 1 at slow speed was 76 MPa which indicates that the material requires a low to moderate force to deform. The yield pressure for Form 3 at slow speed was 109 MPa which indicates that the material requires a greater force to deform.

Strain rate sensitivity (SRS) measures any change in compression behaviour at production compression speeds. The yield pressure at fast speed for Form 1 increased to 89 MPa and Form 3 increased to 140 MPa. The results show a SRS of +16.5% (Form 1) and 29.1% (Form 3). Both forms show a difference in deformation as speed increases and could therefore show difference in compression on scale-up. To achieve the same level of compression at fast speed, an increase in force is required. For both forms here was no evidence of sticking on either the punch or the die wall.

The compaction results reveal that Form 3 has a moderate yield pressure in an ideal range for tablets (80-120 MPa).

Storage at High Humidity and/or Elevated Temperature

A sample of Example 3 (Form 3) was stored at 25° C. and 97% RH for 7 days. Although no decomposition was evident by $^1$H-NMR, XRPD showed that Form 3 had converted at this very high humidity level to Form 1.

A sample of Example 3 (Form 3) was stored at 40° C. and 75% RH for 7 days. Analysis by $^1$H-NMR indicated that some decomposition had occurred under these conditions, Similar decomposition was also observed under these conditions for Form 1.

Example 7: Preliminary Stability Study of Form 3

Analysis of samples of sulforaphane:alpha-cyclodextrin complexes as prepared herein were carried out by HPLC according to the following method:

Column—Phenomenex Gemini C18, 5 μm, 110 Å, 250×4.6 mm;
Mobile Phase A: Water (+0.1% TFA);
Mobile Phase B: Acetonitrile (+0.1% TFA);
Flow: 1.5 mL/min;
Injection Volume: 10 μL;
Column Temperature: 25° C.;
Run Time: 40 minutes;
Sample preparation—Accurately weighed and transferred about 320 mg±30 mg of the sample to a 25-mL volumetric flask, added about 15 mL of diluent (70% water, 30% acetonitrile, 0.1% TFA) and mixed until dissolved. Diluted to volume with diluent and mixed. Transferred 3-4 mL to a syringe and filtered using a 0.45 PTFE filter, discarding the first 1-2 ml, and filtered into an autosampler vial and sealed with PTFE lined cap (prepared in duplicate);
HPLC Gradient according to Table 12

TABLE 12

| Time (min.) | % A (Solvent A) | % B (Solvent B) | Flow (mL/min.) |
|---|---|---|---|
| 0.00 | 95 | 5 | 1.50 |
| 10.00 | 80 | 20 | 1.50 |
| 30.00 | 0 | 100 | 1.50 |
| 32.00 | 0 | 100 | 1.50 |
| 32.10 | 95 | 5 | 1.50 |
| 40.00 | 95 | 5 | 1.50 |

Sulforaphane and certain related impurity peaks are summarised in Table 13, Characterisation of the impurities was carried out by LC-MS and $^1$H-NMR. Relative Retention Times (RRT) are based on the HPLC method described above.

TABLE 13

| Peak | HPLC RRT | MW | Reference | Structure |
|---|---|---|---|---|
| 1 | 0.56 | 312 | Dimer | 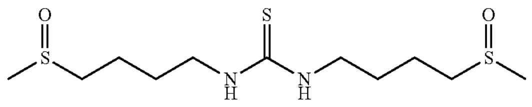 |
| 2 | 0.60 | 1151 | α-CD adduct | Not confirmed |
| 3 | 1.00 | 177 | Sulforaphane | 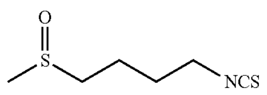 |
| 4 | 1.14 | 296 | Mixed dimer | 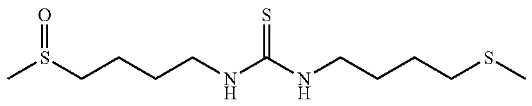 |
| 5 | 1.21 | 193 | Erysolin | 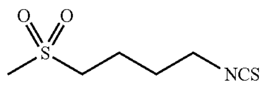 |

TABLE 13-continued

| Peak | HPLC RRT | MW | Reference | Structure |
|---|---|---|---|---|
| 6 | 1.58 | 280 | Thioether dimer | 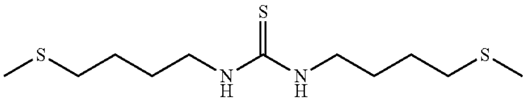 |

Samples of Form 1 (batch ref. LS19-0004-S-8002), Form 3 prepared by minimally-agitated drying (Example 5.3; batch ref. 491-PAL-18) and Form 3 prepared by continuously-agitated filter drying (Example 5B—trial 5; batch ref. 00173-005) were stored at 5° C. (Table 14) and at 25° C./60% RH (Table 15) for 8 weeks in 60 ml Duma® bottles fitted with 45 mm Duma® caps and samples were analysed by HPLC according to the above method.

TABLE 14

| Related substances (% Area); 5° C. stability | | | | | | | |
|---|---|---|---|---|---|---|---|
| | Time | HPLC RRT | | | | | Total |
| Sample | Point | 0.56 | 0.60 | 1.14 | 1.21 | 1.58 | Impurities |
| Form 3 (Example 5.3) | Initial | <0.05 | 0.95 | 0.05 | 0.29 | 0.08 | 1.71 |
| | 8 wk | <0.05 | 1.19 | 0.05 | 0.28 | 0.07 | 1.98 |
| Form 3 (Example 5B-trial 5) | Initial | 0.15 | 0.36 | <0.05 | 0.28 | <0.05 | 1.16 |
| | 8 wk | 0.15 | 0.42 | 0.05 | 0.29 | <0.05 | 1.30 |

TABLE 15

| Related substances (% Area); 25° C./60% RH stability | | | | | | | |
|---|---|---|---|---|---|---|---|
| | Time | HPLC RRT | | | | | Total |
| Sample | Point | 0.56 | 0.60 | 1.14 | 1.21 | 1.58 | Impurities |
| Form 1 (LS19-0004-S-8002) | Initial | 0.19 | 0.06 | <0.05 | 0.28 | <0.05 | 0.90 |
| | 8 wk | 0.20 | 0.10 | 0.06 | 0.30 | <0.05 | 0.99 |
| Form 3 (Example 5.3) | Initial | <0.05 | 0.95 | 0.05 | 0.29 | 0.08 | 1.71 |
| | 8 wk | 0.26 | 3.21 | 0.05 | 0.27 | 0.07 | 4.57 |
| Form 3-(Example 5B trial 5) | Initial | 0.15 | 0.36 | <0.05 | 0.28 | <0.05 | 1.16 |
| | 8 wk | 0.28 | 1.15 | 0.06 | 0.28 | <0.05 | 2.35 |

It should be noted that the 'initial' timepoint does not refer to immediately after synthesis, but rather just to the start of the respective stability study (e.g. the Example 5B—trial 5 sample had been refrigerated and stored post-synthesis for 5-6 months prior to initiation of the stability study). This preliminary (8 week) stability study is not, therefore, a full side-by-side study of samples prepared at the same time and stored under equivalent conditions.

Example 7B: Water Content of Stability Samples

The water content of samples of Form 1 (batch ref. LS19-0004-3-8002), Form 3 prepared by minimally-agitated drying (Example 5B; batch ref. 491-PAL-18) and Form 3 prepared by continuously-agitated filter drying (Example 5B trial 5; batch ref. 00173-005) was analysed by KF at the start of the stability study (initial) and after 2, 4 and 8 weeks storage in 60 ml Duma® bottles fitted with 45 mm Duma® caps (without desiccant) at 25° C./60% RH—see Table 16;

TABLE 16

| | KF water content (% w/w) | | | |
|---|---|---|---|---|
| | Initial | 2 weeks | 4 weeks | 8 weeks |
| Form 1 (LS19-0004-S-8002) | 8.6 | 8.4 | 6.5 | 11.1 |
| Form 3 (Example 5.3) | 2.4 | 2.5 | 2.1 | 3.2 |
| Form 3 (Example 5B - trial 5) | 2.9 | 3.3 | 2.6 | 3.6 |

In a separate study, samples of Form 3 (Example 5.3; batch ref. 491-PAL-18) having an initial water content by KF of 2.3% w/w were tested for water content at various time points after storage double bagged in a HDPE bottle under various conditions as shown in Table 17.

TABLE 17

| | KF water content (% w/w) | | | |
|---|---|---|---|---|
| Storage Conditions | Initial | 1 month | 3 months | 6 months |
| 5° C. | 2.3 | 4.2 | 4.6 | 4.7 |
| 25° C./60% RH | 2.3 | 6.1 | 5.7 | 6.1 |
| 40° C./75% RH | 2.3 | 6.2 | 6.2 | — |

In general it can be seen from the above data that although over-dried Form 3 (e.g. less than 4% w/w water) has a tendency to take up water, the water content does not increase significantly above about 5-6% w/w; even when Form 3 material is exposed to high levels of humidity for extended periods such as up to 6 months.

FIG. 23 shows an overlay of XRPD plots for the 1 month (40° C./75% RH) and 3 month (25° C./60% RH) samples from this study and it can be seen that the main peaks are concordant with Form 3 (10.7±0.2° 2θ).

Example 8: Chemical Stability of Form 1 & Form 3 in Biorelevant Media

Samples of Form 1 (batch ref L17-0004-S-8002) and Form 3 (Example 5.4.1 (batch ref. 491PAL22; A-19-0132)) in 0.1 M HCl and FaSSIF media (1.2 mg/ml) were stored at ambient and 37° C. for up to 7 days. Chemical stability was assessed by determining the concentration of parent compound by HPLC on days 0, 3 and 7 in triplicate.

TABLE 18

| | | Day 0 | | Day 3 | | Day 7 | |
|---|---|---|---|---|---|---|---|
| Form | Media | Mean Conc (mg/ml) | Std Dev | Mean Conc (mg/ml) | Std Dev | Mean Conc (mg/ml) | Std Dev |
| 1 | 0.1M HCl, ambient | 1.22 | 0.03 | 1.09 | 0.04 | 1.05 | 0.03 |
| | 0.1M HCl, 37° C. | 1.18 | 0.01 | 1.06 | 0.04 | 1.05 | 0.03 |
| | FaSSIF, ambient | 1.16 | 0.02 | 0.96 | 0.01 | 0.90 | 0.07 |
| | FaSSIF 37° C. | 1.18 | 0.04 | 0.92 | 0.04 | 0.94 | 0.07 |
| 3 | 0.1M HCl, ambient | 1.08 | 0.03 | 0.94 | 0.03 | 1.01 | 0.00 |
| | 0.1M HCl, 37° C. | 1.05 | 0.00 | 0.94 | 0.02 | 0.92 | 0.06 |
| | FaSSIF, ambient | 1.00 | 0.01 | 0.81 | 0.02 | 0.93 | 0.01 |
| | FaSSIF, 37° C. | 1.01 | 0.02 | 0.80 | 0.02 | 0.78 | 0.02 |

The data in Table 18 shows that whilst some loss of parent was observed under acidic media, there is approximately 1.5 times more loss of parent in FaSSIF over the same time period, Little difference was observed between Forms 1 and 3 in terms of % loss of parent.

Example 9: Equilibrium Solubility of Form 1 & Form 3 in Biorelevant Media

The equilibrium solubility of samples of Form 1 (batch ref L17-0004-S-8002) and Form 3 (Example 5.4.1 (batch ref, 491PAL22; A-19-0132)) in 0.1M HCl and FaSSIF media at 37° C. was carried out using the shake flask method. Samples were taken at 4 hours and 24 hours and centrifuged for 5 minutes at 15,000 rpm. The supernatant was removed and diluted with appropriate solvent prior to HPLC analysis of the parent concentrations. Samples generated in FaSSIF resulted in atypical HPLC data and variable results.

TABLE 19

| | | 4 Hours | | 24 Hours | |
|---|---|---|---|---|---|
| Form | Media | Mean Conc (mg/ml) | Std Dev | Mean Conc (mg/ml) | Std Dev |
| 1 | 0.1M HCl | 632 | 532 | 2605 | 187 |
| | FaSSIF | 271 | N/A | 247 | N/A |
| 3 | 0.1M HCl | 733 | 442 | 3057 | 14 |
| | FaSSIF | 264 | N/A | 221 | N/A |

Although some variability in the equilibrium solubility of Form 1 and Form 3 was observed, the data in Table 19 demonstrates the solubility of both forms was high and comparable (within experimental error) in both 0.1 M HCl and FaSSIF media. The solubility was higher in the acidic versus FaSSIF media for both forms.

Example 10: Kinetic Solubility of Form 1 & Form 3 in Biorelevant Media

A small-scale kinetic solubility study was carried out at a nominal concentration of 200-400 mg/ml to ensure solid material remained at the end of the experiment for XRPD analysis. Approximately 100 mg of sample—Form 1 (batch ref L17-0004-S-8002) or Form 3 (Example 5.4.1 (batch ref. 491PAL22; A-19-0132)) was weighed into a 1 ml vial and 250 μl of 0.1 M HCl was added to the vial for the 15 and 30 minute timepoints and 500 μl of a 1:1 mixture of 0.1 M HCl and FaSSIF was added to the vial for the 60 and 180 minute timepoints, The vial was agitated and maintained at 37° C.

The study was carried out in duplicate. Each sample was centrifuged to remove suspended solids. An aliquot of the supernatant was transferred to a second vial for further centrifugation and then transferred to an LC vial, diluted with an appropriate solvent and analysed by HPLC for parent compound. The residual solids were analysed by XRPD.

TABLE 20

| | Mean conc (mg/ml) | | | |
|---|---|---|---|---|
| Form | 15 mins (simulated gastric) | 30 mins (simulated gastric) | 60 mins (simulated intestinal) | 180 mins (simulated intestinal) |
| 1 | 319 | 318 | 191 | 180 |
| 3 | 298 | 298 | 171 | 157 |
| XRPD analysis | Form 1 for both samples | Form 1 for both samples | Form 1 for Form 1 sample & Mixture of Forms 1 & 3 for Form 3 sample | Form 1 for Form 1 sample & Mixture of Forms 1 & 3 for Form 3 sample |

As shown by the Table 20 data, both Form 1 and Form 3 dissolve rapidly in 0.1 M HCl achieving approximately 300 mg/ml by the 15 minute timepoint. A pH shift, to represent the transit from gastric to intestinal environments resulted in a drop in parent concentration to approximately 180 mg/ml at the 60 minute and 180 minute timepoints. The XRPD analysis of the residual solids indicates that Form 1 or a mixture of Forms 1 & 3 was observed at the end of the study.

The invention claimed is:

1. A crystalline complex of sulforaphane and alpha-cyclodextrin having a water content of less than 8% w/w, wherein the crystalline form of the complex is stable between 0% and 60% relative humidity at 25° C.

2. The crystalline complex according to claim 1 having a water content of less than 6% w/w.

3. The crystalline complex according to claim 1, wherein the molar ratio of sulforaphane to alpha-cyclodextrin in the complex is in the range 0.9:1 to 1.1:1.

4. The crystalline complex according to claim 1, wherein the molar ratio of sulforaphane to alpha-cyclodextrin in the complex is about 1:1.

5. A crystalline complex of sulforaphane and alpha-cyclodextrin (Form 3), wherein the crystalline form of the complex is characterized by XRPD peaks at 5.3 and 10.7±0.2° 2θ, when measured in reflection mode.

6. The crystalline complex according to claim 5, further characterized by further XRPD peaks at 8.1 and 16.1±0.2° 2θ, when measured in reflection mode.

7. The crystalline complex according to claim 5 that exhibits an X-ray powder diffraction pattern substantially the same as the X-ray powder diffraction pattern shown in FIG. 4 when measured at room temperature using Cu Kα radiation.

8. The crystalline complex according to claim 1, wherein the complex comprises less than 5% w/w of particles greater than 2000 μm in diameter.

9. A method for forming a crystalline complex of sulforaphane and alpha-cyclodextrin according to claim 1, the method comprising the steps:

a) providing a complex of sulforaphane and alpha-cyclodextrin;

b) drying the complex from step a) with agitation of the complex at a pressure of less than 200 mbar, until the water content of the complex is less than 6% w/w.

10. A solid pharmaceutical composition comprising an effective amount of the crystalline complex according to claim 1, and optionally at least one pharmaceutically acceptable excipient.

11. The solid pharmaceutical composition according to claim 10, wherein greater than 50% of the crystalline complex of sulforaphane and alpha-cyclodextrin is characterized by XRPD peaks at 5.3 and 10.7±0.2° 2θ, when measured in reflection mode.

12. The solid pharmaceutical composition according to claim 10, wherein greater than 80% of the crystalline complex of sulforaphane and alpha-cyclodextrin is characterized by XRPD peaks at 5.3 and 10.7±0.2° 2θ, when measured in reflection mode.

13. The solid pharmaceutical composition according to claim 10, wherein the composition is formulated as a tablet or a capsule.

14. A combination comprising a complex according to claim 1 and one or more additional therapeutic agents.

15. The combination according to claim 14, wherein the one or more additional therapeutic agents are selected from an aromatase inhibitor, tamoxifen, exemestane, fulvestrant, an oral SERD and a CDK4/6 inhibitor.

* * * * *